(12) United States Patent
Shi et al.

(10) Patent No.: US 11,638,771 B2
(45) Date of Patent: May 2, 2023

(54) APPARATUS AND METHOD FOR DELIVERING A VOLATILE MATERIAL

(71) Applicant: The Procter & Gamble Company, Cincinnati, OH (US)

(72) Inventors: Gui Min Shi, Singapore (SG); Tai-Shung Chung, Singapore (SG); Bee Ting Low, Singapore (SG); Calum Macbeath, Singapore (SG)

(73) Assignee: The Procter & Gamble Company, Cincinnati, OH (US)

( * ) Notice: Subject to any disclaimer, the term of this patent is extended or adjusted under 35 U.S.C. 154(b) by 455 days.

(21) Appl. No.: 16/744,272

(22) Filed: Jan. 16, 2020

(65) Prior Publication Data
US 2020/0254129 A1   Aug. 13, 2020

Related U.S. Application Data

(63) Continuation of application No. PCT/US2018/049816, filed on Sep. 7, 2018.

(60) Provisional application No. 62/555,658, filed on Sep. 8, 2017.

(51) Int. Cl.
*A61L 9/12* (2006.01)

(52) U.S. Cl.
CPC .......... *A61L 9/12* (2013.01); *A61L 2209/131* (2013.01)

(58) Field of Classification Search
CPC ......... A61L 9/12; A61L 2209/131; A61L 9/03
See application file for complete search history.

(56) References Cited

U.S. PATENT DOCUMENTS

| 2010/0264232 A1* | 10/2010 | Gruenbacher ............ A61L 9/04 239/6 |
| 2019/0046926 A1* | 2/2019 | Laleg ...................... C02F 1/008 |
| 2019/0307912 A1* | 10/2019 | Santini ..................... A61L 9/03 |

FOREIGN PATENT DOCUMENTS

| WO | WO0072951 A1 | 12/2000 |
| WO | WO2010120960 A1 | 10/2010 |

OTHER PUBLICATIONS

AA1257 Search Report; PCT/US2018/049816; dated Nov. 29, 2018; 13 Pages.

* cited by examiner

*Primary Examiner* — Sean E Conley
*Assistant Examiner* — Brendan A Hensel
(74) *Attorney, Agent, or Firm* — George H. Leal; Abbey A. Lopez

(57) ABSTRACT

Apparatus for delivering a volatile material including a reservoir with an opening for containing a volatile material. A first membrane is disposed adjacent the opening of the reservoir, and a second membrane disposed adjacent the opening such that the first membrane is disposed between the second membrane and the reservoir, wherein at least a portion of the second membrane is spaced apart from the first membrane forming a vapor chamber between the first and second membranes.

12 Claims, 15 Drawing Sheets

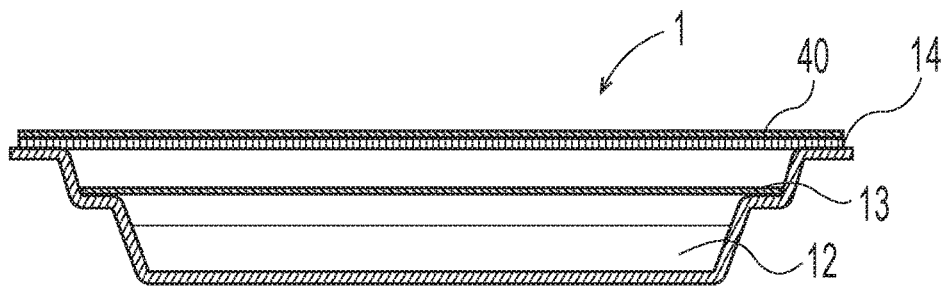
Fig. 5
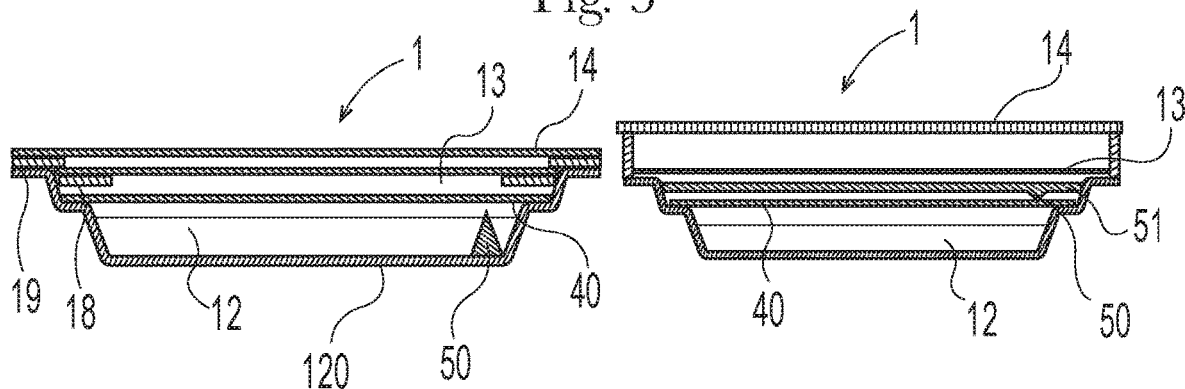
Fig. 6
Fig. 7
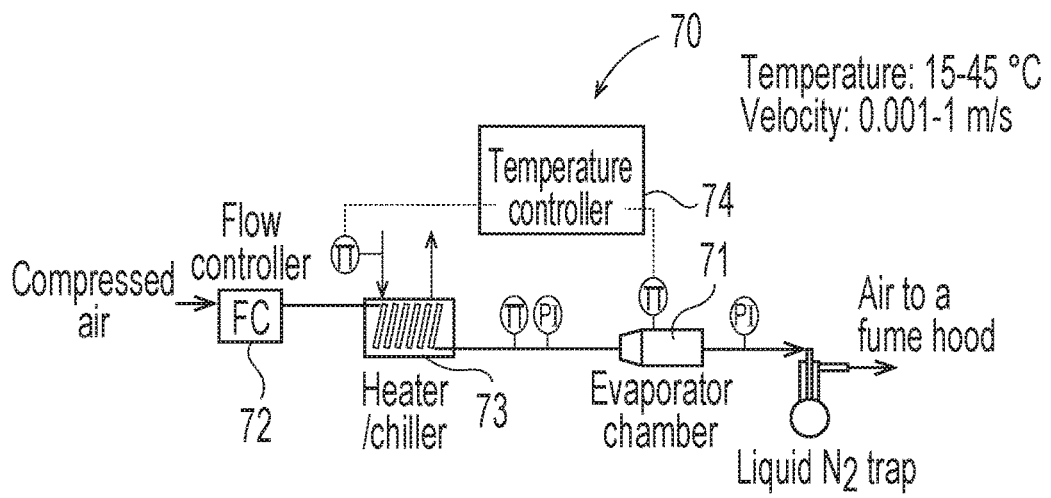
Fig. 8

FIG. 11

Comparative Sample J

| Time, (h) | 3.0 | 5.3 | 21.1 | 28.6 | 50.9 | 93.0 | 142.3 | 166.0 | 190.1 | 263.4 | 357.9 | 407.2 | 429.7 | 455.5 | 502.1 | 526.3 | 622.4 | 655.0 | 698.7 | 771.9 |
|---|---|---|---|---|---|---|---|---|---|---|---|---|---|---|---|---|---|---|---|---|
| Vapor Release Rate (mg/cm2-h) | 5.55 | 4.47 | 1.97 | 0.81 | 0.38 | 0.33 | 0.25 | 0.32 | 0.26 | 0.19 | 0.14 | 0.11 | 0.12 | 0.08 | 0.07 | 0.07 | 0.07 | 0.05 | 0.04 | |

Inventive Sample A

| Time, (h) | 3.5 | 5.0 | 21.4 | 28.7 | 45.8 | 93.8 | 143.0 | 166.4 | 191.4 | 262.1 | 358.1 | 390.8 | 410.4 | 434.7 | 507.7 | 526.3 | 555.5 | 603.6 | 668.8 | 698.7 | 724.8 |
|---|---|---|---|---|---|---|---|---|---|---|---|---|---|---|---|---|---|---|---|---|---|
| Vapor Release Rate (mg/cm2-h) | 1.56 | 1.83 | 1.39 | 0.95 | 0.85 | 0.19 | 0.13 | 0.1 | 0.08 | 0.09 | 0.09 | 0.09 | 0.1 | 0.09 | 0.08 | 0.07 | 0.07 | 0.08 | 0.07 | 0.07 | 0.07 |

| Time, (h) | 0.00 | 2.10 | 4.08 | 6.05 | 24.82 | 71.02 | 95.15 | 119.23 | 143.88 | 167.13 | 239.55 |
|---|---|---|---|---|---|---|---|---|---|---|---|
| Ethyl-2-methyl butyrate concentration, wt% | 23.43 | 23.03 | 18.79 | 16.75 | 5.90 | 1.34 | 1.18 | 0.00 | 0.00 | 0.00 | 0.00 |
| Benzyl acetate concentration, wt% | 25.07 | 28.52 | 27.02 | 27.79 | 33.09 | 29.80 | 29.32 | 28.50 | 27.41 | 25.19 | 21.19 |
| Phenyl ethyl alcohol concentration, wt% | 24.19 | 27.26 | 25.82 | 26.73 | 32.95 | 32.07 | 33.28 | 33.97 | 33.84 | 32.93 | 32.82 |
| Cyclamen aldehyde concentration, wt% | 27.32 | 21.20 | 28.37 | 28.73 | 28.06 | 36.80 | 37.35 | 37.54 | 38.75 | 41.88 | 45.23 |

| | Time, h | 2.57 | 4.60 | 6.63 | 25.35 | 71.43 | 78.27 | 95.62 | 102.28 | 119.77 | 144.42 | 167.55 | 239.80 | 263.80 | 288.12 |
|---|---|---|---|---|---|---|---|---|---|---|---|---|---|---|---|
| Inventive Sample B | Vapor Release Rate (mg/cm2-h) | 3.28 | 3.18 | 3.09 | 1.83 | 0.60 | 0.31 | 0.19 | 0.16 | 0.13 | 0.09 | 0.11 | 0.10 | 0.13 | 0.08 |
| Inventive Sample C | Time, h | 2.33 | 4.35 | 6.42 | 25.12 | 71.18 | 78.02 | 95.37 | 102.05 | 119.53 | 144.18 | 167.32 | 239.57 | 263.57 | 287.88 |
| | Vapor Release Rate (mg/cm2-h) | 4.10 | 3.83 | 3.48 | 1.90 | 0.51 | 0.26 | 0.16 | 0.14 | 0.12 | 0.09 | | | | |
| Inventive Sample D | Time, h | 2.17 | 4.18 | 6.23 | 24.95 | 71.03 | 77.85 | 95.20 | 101.88 | 119.37 | 144.00 | | 239.57 | 263.57 | |
| | Vapor Release Rate (mg/cm2-h) | 3.93 | 3.70 | 3.26 | 1.52 | 0.30 | 0.19 | 0.12 | 0.10 | 0.10 | 0.08 | 0.11 | 0.11 | 0.14 | 0.09 |

FIG. 16

Inventive Sample B

| Time, (h) | 0.00 | 2.08 | 4.07 | 6.08 | 24.88 | 71.05 | 95.18 | 119.27 | 143.90 | 167.13 | 239.58 |
|---|---|---|---|---|---|---|---|---|---|---|---|
| Ethyl-2-methyl butyrate concentration, wt% | 23.43 | 20.54 | 19.11 | 17.32 | 7.86 | 1.79 | 1.31 | 0.05 | 0.00 | 0.00 | 0.00 |
| Benzyl acetate concentration, wt% | 25.07 | 25.50 | 26.15 | 26.82 | 31.01 | 31.96 | 30.33 | 30.64 | 29.99 | 26.62 | 26.57 |
| Phenyl ethyl alcohol concentration, wt% | 24.19 | 24.39 | 25.04 | 25.68 | 30.28 | 32.69 | 31.82 | 32.86 | 32.88 | 32.59 | 32.21 |
| Cyclamen aldehyde concentration, wt% | 27.32 | 29.57 | 29.70 | 30.17 | 30.85 | 33.56 | 36.54 | 36.44 | 37.13 | 38.79 | 41.22 |

Inventive Sample C

| Time, (h) | 0.00 | 2.17 | 4.07 | 6.07 | 24.87 | 71.08 | 95.18 | 119.30 | 143.88 | 167.12 | 239.55 |
|---|---|---|---|---|---|---|---|---|---|---|---|
| Ethyl-2-methyl butyrate concentration, wt% | 23.43 | 22.78 | 19.26 | 18.23 | 9.52 | 2.36 | 1.52 | 1.30 | 0.04 | 0.00 | 0.00 |
| Benzyl acetate concentration, wt% | 25.07 | 27.41 | 26.71 | 26.48 | 29.95 | 32.22 | 31.80 | 31.51 | 29.69 | 29.36 | 27.10 |
| Phenyl ethyl alcohol concentration, wt% | 24.19 | 26.17 | 24.66 | 25.33 | 29.13 | 32.59 | 32.97 | 33.35 | 31.84 | 32.23 | 31.35 |
| Cyclamen aldehyde concentration, wt% | 27.32 | 23.64 | 30.37 | 29.95 | 31.40 | 32.82 | 33.70 | 33.84 | 38.41 | 38.41 | 41.55 |

Inventive Sample D

| Time, (h) | 0.00 | 2.05 | 4.00 | 5.98 | 24.77 | 70.98 | 95.10 | 119.40 | 143.80 | 167.02 | 239.45 |
|---|---|---|---|---|---|---|---|---|---|---|---|
| Ethyl-2-methyl butyrate concentration, wt% | 23.43 | 22.32 | 21.21 | 18.65 | 10.80 | 2.55 | 1.66 | 1.33 | 0.07 | 0.00 | 0.00 |
| Benzyl acetate concentration, wt% | 25.07 | 25.66 | 26.14 | 26.20 | 31.14 | 30.47 | 31.96 | 32.10 | 30.25 | 30.75 | 22.17 |
| Phenyl ethyl alcohol concentration, wt% | 24.19 | 24.60 | 24.66 | 25.19 | 30.42 | 31.14 | 32.96 | 33.72 | 32.33 | 33.43 | 25.38 |
| Cyclamen aldehyde concentration, wt% | 27.32 | 27.42 | 27.99 | 29.95 | 27.64 | 35.85 | 33.41 | 32.85 | 37.35 | 35.81 | 52.45 |

APPARATUS AND METHOD FOR DELIVERING A VOLATILE MATERIAL

FIELD OF THE INVENTION

The present invention relates to an apparatus and a method for delivering a volatile material to the atmosphere, and more particularly, relates to an apparatus and a method delivering a volatile material using two spaced apart membranes to create a vapor chamber between the membranes.

BACKGROUND OF THE INVENTION

Devices for dispensing volatile materials are well known and commonly used to deliver a variety of benefits such as freshening, malodor removal or scenting of air in spaces in household and commercial establishments such as rooms, or enclosed spaces such as a vehicle passenger compartment space. For example, air freshening products have been designed for dispensing volatile materials such as a volatile composition comprising one or more volatile materials like perfume oils. The volatile composition may be contained in, for example, a spray bottle and be sprayed into the air of interior spaces as droplets which transition to vapor. However, such products do not continuously freshen (i.e., the volatile composition is only dispensed upon manual activation). Alternatively, volatile compositions may be dispensed through systems which do not require manual actuation such as via evaporating the volatile composition from membrane based, wick based and gel based systems.

However, a problem with such air freshening products is often an inconsistency in the evaporation rate of the volatile composition over the product life, i.e. high evaporation rate of the volatile composition at the beginning of product use and low evaporation rate towards end of product life. Specifically, the volatile composition typically comprises a mixture of highly volatile compounds and other volatile compounds which are less volatile ("less volatile compounds"). Highly volatile compounds generally have higher vapor pressures than the less volatile compounds. Specifically, at a given temperature, a highly volatile compound with a higher vapor pressure vaporizes more readily than a less volatile compound with a lower vapor pressure. In use, the highly volatile compounds tend to evaporate more quickly at the beginning of such a product's use, while the less volatile compounds evaporate later, resulting in an overall inconsistent scent intensity and fragrance character of the volatile composition over the product life. The high initial evaporation rate can result in an overpowering initial scent intensity which can create a perception that the air freshener product has a different scent intensity over the product life or that the product is no longer effective after the initial scent intensity is no longer present. Therefore, there exists a need for an apparatus for delivering volatile materials at a reduced initial evaporation rate and scent intensity. There is also a need for an apparatus and method to provide a consistent evaporation rate, scent intensity and/scent character over time.

SUMMARY OF THE INVENTION

The present invention relates to an apparatus for delivering a volatile material comprising:
a reservoir for containing a volatile material, the reservoir including an opening;
a first membrane disposed adjacent the opening of the reservoir; and
a second membrane disposed adjacent the opening of the reservoir such that the first membrane is disposed between the reservoir and the second membrane, wherein at least a portion of the second membrane is spaced apart from the first membrane forming a vapor chamber between the first and second membranes.

BRIEF DESCRIPTION OF THE DRAWINGS

FIG. 5 is a cross-sectional view of a vapor impermeable substrate arranged in an apparatus for delivering a volatile material according to the present invention;

FIG. 6 is a cross-sectional view of a vapor impermeable substrate and a rupture element arranged in an apparatus for delivering a volatile material according to the present invention;

FIG. 7 is a cross-sectional view of an alternative arrangement of a vapor impermeable substrate and a rupture element arranged in an apparatus for delivering a volatile material according to the present invention;

FIG. 8 is a flow schematic diagram illustrating an air freshener testing system for use in the Vapor Release Rate Test Method (Chamber method) described hereinafter;

FIG. 11 illustrates Table 9 which reports vapor release rates of volatile materials released from Comparative Sample A and an apparatus for delivering a volatile material according to the present invention ("Inventive Sample A") as a function of time;

FIG. 16 illustrates Table 12 which reports vapor release rates of volatile materials released from apparatuses with second membranes of different pore sizes according to the present invention ("Inventive Samples B, C, D") as a function of time;

DETAILED DESCRIPTION OF THE INVENTION

Figure 1A:
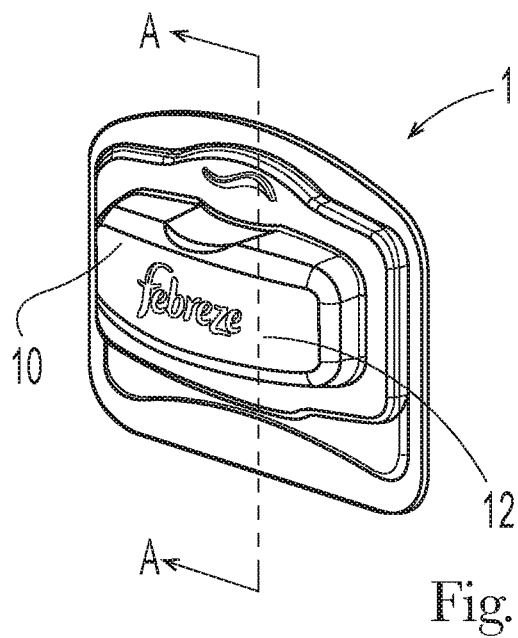
FIG. 1A is a perspective view of an apparatus for delivering a volatile material according to the present invention.

The present invention relates to an apparatus and method for the delivery of a volatile material to the atmosphere in a continuous manner. Specifically, the apparatus comprises a reservoir for receiving a liquid phase or solid phase of the volatile material and a vapor chamber for receiving a vapor phase of the volatile material. Two or more membranes are arranged in the apparatus to create the reservoir and the vapor chamber such that the liquid or solid phase of the volatile material is physically separated from the vapor phase, thereby enabling a controlled release of the vapor phase of the volatile material from the apparatus through one of the membranes. For example, if the volatile material in the reservoir is in a solid phase, the vapor phase may be transported across a first membrane followed by transportation across a second membrane of the apparatus. Alternatively, if the reservoir contains a volatile material in the form of a gel with liquid perfume, both a liquid phase (i.e. liquid perfume in gel) and/or a vapor phase (liquid perfume from gel vaporizes) of the volatile material may be transported across the first membrane.

In the following description, the apparatus described is a consumer product, such as an air freshener, for evaporating a volatile material in spaces to deliver a variety of benefits such as freshening, malodor removal or scenting of air in spaces such as rooms in household and commercial establishments, or enclosed spaces such as a vehicle passenger compartment space. However, it is contemplated that the apparatus may be configured for use in a variety of applications to deliver volatile materials to the atmosphere and the apparatus may include but is not limited to consumer products, such as, for example air freshening products.

Prior to describing the present invention in detail, the following terms are defined for clarity. Terms not defined should be given their ordinary meaning as understood by a skilled person in the relevant art.

"Horizontal orientation" as used herein, refers to a position of an apparatus according to the present invention wherein the second membrane is facing the environment in an upward or downward position.

"Vertical orientation" as used herein, refers to a position of an apparatus according to the present invention wherein the second membrane is facing the environment in a forward facing position or in a rear facing position.

"Mean free path ($\lambda$)" as used herein, refers to a mean free path of vapor of the volatile material wherein the mean free path is determined based on Formula (1) below which is presented in Benitez, J. Principle and Modern Applications of Mass Transfer Operations, Wiley, 2009.

$$\lambda = \frac{k_b T}{\sqrt{2}\, \pi d^2 P} \tag{1}$$

Where $k_b$, the Boltzman constant, is $1.38*10^{-23}$. P is the pressure in Pa and d is the kinetic diameter of the vapor molecule of a volatile component/compound of the volatile material that permeates the second membrane.

"Mean pore size" as used herein, refers to a volume average diameter of pores of a membrane, wherein the mean pore size is determined in accordance with the Mean Pore Size Test Method specified herein. Alternatively, "Mean pore size" may also include pore radius of pores of a membrane, wherein the mean pore size is determined in accordance with the Pore Size Calculation Method specified herein.

"Mean thickness" as used herein, refers to an average thickness of a membrane as measured in accordance with the Mean Thickness Test Method specified herein.

"Membrane" as used herein, refers to a semi-permeable material which allows some components of matter to pass through but stops other components. Of the components that pass through, the membrane moderates the permeation of components i.e. some components permeate faster than other components. Such components may include molecules, ions or particles.

"Microporous membrane" as used herein, refers to a material having a network of pores.

"Non-energized" as used herein, means that the apparatus is passive and does not require to be powered by a source of external energy. In particular, the apparatus does not need to be powered by a source of heat, gas, or electrical current, and the volatile composition is not delivered by aerosol means. Further, as used in this specification and the appended claims, the singular forms "a", "an", and "the" include plural references unless the content clearly dictates otherwise.

"Porosity" as used herein, refers to the void volume of a material, expressed as percent by volume, and is determined according to the Porosity Test Method specified herein.

"Top notes" as used herein, refer to perfume raw materials having a high volatility.

"Bottom notes" as used herein, refer to perfume raw materials which are less volatile relative to the top notes.

"Vapor" as used herein, refers to a gaseous form of an organic or inorganic substance which coexists as a solid or liquid at ambient conditions including but not limited to temperature, humidity and air pressure.

"Vapor impermeable substrate" as used herein, refers to a material configured to resist diffusion of vapor from the apparatus prior to its intended use.

"Vapor release rate" as used herein, refers to a measure of the passage of vapor through a substrate.

"Volatile material" as used herein, refers to a material that is vaporizable at room temperature and atmospheric pressure without the need of an energy source. The volatile material may be a composition comprises entirely of a single volatile material or entirely of a volatile material mixture (i.e. the mixture has more than one volatile component). Further, it is not necessary for all of the component materials of the composition to be volatile. Any suitable volatile material in any amount or form, including a liquid, solid, or emulsion, may be used. Materials suitable for use herein may include non-volatile compounds, such as carrier materials (e.g., water, solvents, etc.). It should also be understood that when the volatile material is described herein as being "delivered", "emitted", or "released", this refers to the volatization of the volatile component thereof, and does not require that the non-volatile components thereof be emitted.

"Wet mode" as used herein, refers to a liquid phase of the volatile material being in contact with at least a part of a membrane.

"Dry mode" as used herein, refers to a vapor phase of the volatile material in contact with at least a part of a membrane.

For the purposes of illustrating the present invention in detail, the invention is described below as a non-energized apparatus. However, the apparatus may be configured for use with an energized device such as, for example, an electrical heating device or a fan.

Figure 1B:
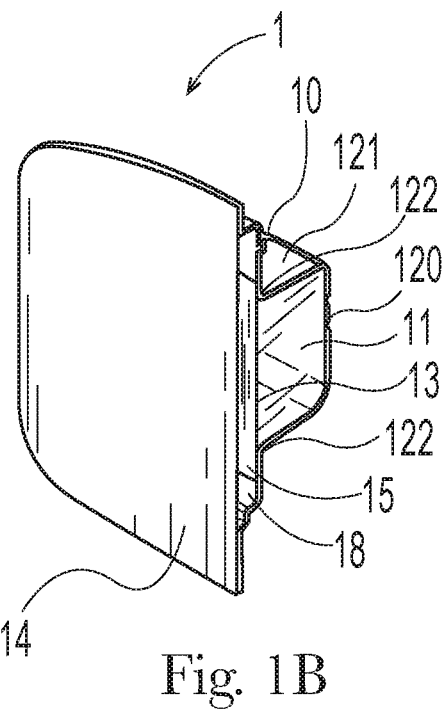
FIG. 1B is a cross-sectional view along lines A-A of the apparatus of FIG. 1A.
Figure 2:
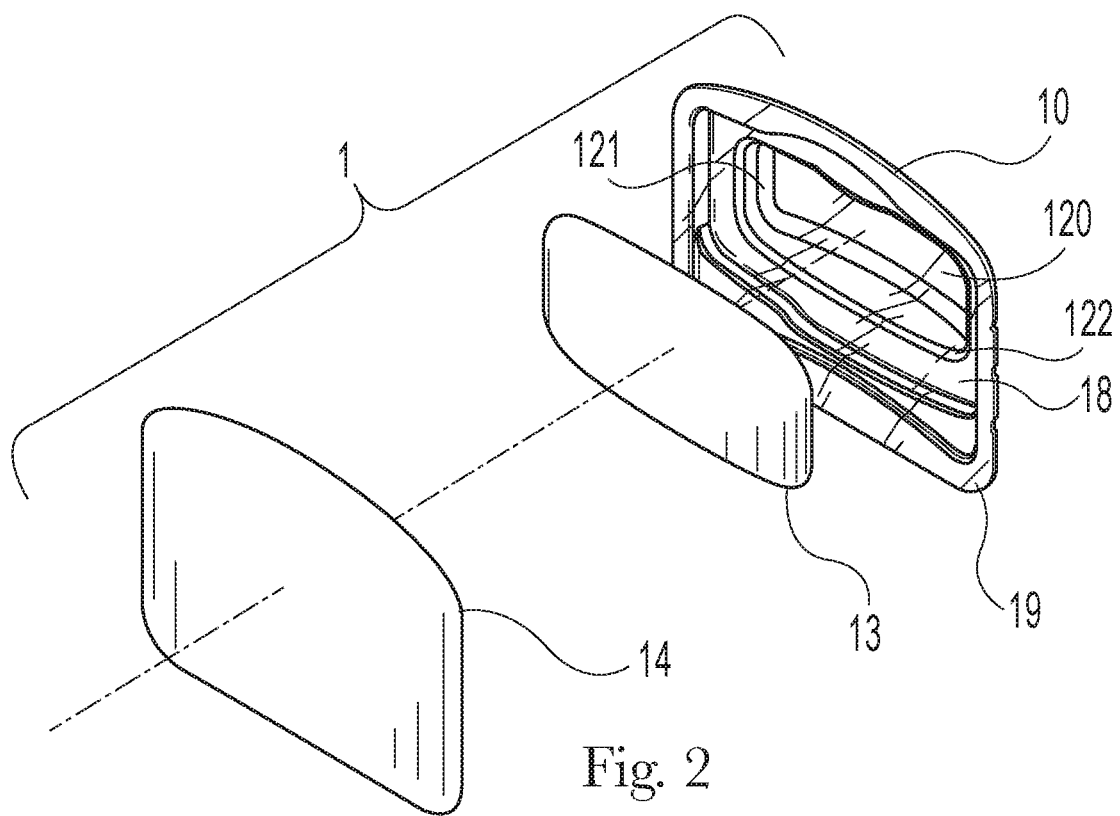
FIG. 2 is a perspective view of components in the apparatus of FIG. 1A.

FIG. 1A is a perspective view of an apparatus 1 for delivering a volatile material according to the present invention. FIG. 1B is a cross-sectional view along lines A-A of the apparatus 1 and FIG. 2 is a perspective view of components in the apparatus 1. The apparatus 1 can be constructed as a disposable, single-use item or one that it is replenished with a volatile material. The apparatus 1 may be configured to be in a vertical orientation during use such as shown in FIGS. 1A and 1B. Alternatively, the apparatus 1 may be configured to be in a horizontal orientation when used such as shown in FIGS. 5, 6 and 7.

Referring to FIGS. 1A and 1B, the apparatus 1 comprises a container 10 comprising a reservoir 11 for containing a volatile material 12. The container 10 may be made of a substantially vapor impermeable substrate designed to resist diffusion of a vapor phase of the volatile material 12 from the apparatus 1 prior to its intended use. For example, the container 10 may be made of metal, glass, ceramic, porcelain, tile and plastic including but not limited to thermoplastics and other known materials suitable for thermoforming, injection molding and blow molding.

Referring to FIG. 1B, the container 10 may comprise an end wall 120, side walls 121 and a first opening at a periphery 122 of the side walls 121 which define the reservoir 11. A first membrane 13 may be disposed within the container 10 adjacent to the reservoir 11, and may be attached to an inner periphery 18 of the container 10 to contain the volatile material 12 within the reservoir 11. A second membrane 14 may be spaced apart from the first membrane 13 forming a vapor chamber 15 between the first and second membranes 13, 14. The first and second membranes 13, 14 comprise pores to allow passage of the volatile material therethrough. The specific physical properties of the first and second membranes 13, 14 may be chosen based on the specific desired use. Examples of suitable physical parameters of the membranes are described in more detail in the following description.

First Membrane

The first membrane 13 may be a thin layer of porous material that is vapor permeable and is designed to be capable of wicking liquid, yet prevents free flow of liquid out of the first membrane 13. Specifically, the first membrane 13 may be a microporous membrane. The mean pore size of the first membrane 13 as determined by the Mean Pore Size Test Method specified herein may be configured based on the particular volatile material 12 in the reservoir 11. For example, the mean pore size of the first membrane 13 may be chosen based on the form or state of the volatile material 12 to be used and/or the rate at which it is desired for the volatile material 12 pass through the first membrane 13. For typical crystalline solids and perfume oils, for example, it has been found that the first membrane 13 may have a mean pore size of about 0.01 to about 1 microns, about 0.01 to about 0.06 microns, from about 0.01 to about 0.05 microns, about 0.01 to about 0.04 microns, about 0.01 to about 0.03 microns, about 0.02 to about 0.04 microns, or about 0.02 microns.

Certain characteristics of the first membrane 13 may be altered by dispersing one or more fillers within the first membrane 13. Fillers can adjust the physical properties of the first membrane 13, such as strength, stiffness, and other tensile properties. There are many known filler and plasticizer materials, including, but not limited to, silica, clays, zeolites, carbonates, charcoals, and mixtures thereof. An example of a filled first membrane 13 is an ultra-high molecular weight polyethylene (UHMWPE) membrane filled with silica, such as those described in U.S. Pat. No.

7,498,369. Although any suitable fill material and weight percentage may be used, typical fill percentages for silica, may be between about 50% to about 80%, about 60% to about 80%, about 70% to about 80%, or about 70% to about 75% of the total weight of the membrane. Examples of suitable membrane thicknesses include, but are not limited to between about 0.01 mm to about 1 mm, between about 0.1 mm to 0.4 mm, about 0.15 mm to about 0.35 mm, or about 0.25 mm.

Second Membrane

The second membrane 14 may comprise the same or different material(s) from the first membrane 13. The second membrane 14 may comprise a material selected from the group consisting of: paper, natural polymers, synthetic polymers and inorganic materials and mixtures thereof.

The second membrane 14 may be chosen and/or configured to have any desired mean pore size, porosity, mean thickness and/or combinations thereof to allow vapor 12B from the volatile material 12 to pass through to the surrounding atmosphere at a desired vapor release rate such as, for example, a vapor release rate of greater than or equal to 0.06 mg/cm$^2$-h and less than or equal to 4 mg/cm$^2$-h.

As with the first membrane 13, there are many different ways to configure the second membrane 14 to have the desired characteristics. Specifically, the thickness, mean pore size and/or porosity of the second membrane 14 may be chosen to provide the desired characteristics. Typically, the second membrane 14 may have a thickness in the range of about 0.001 mm to about 10 mm, a mean pore size of less than about 50,000 nm, and a porosity of between about 0% to about 95% by volume based on the total volume of the second membrane 14, but any one or more of the parameters can be adjusted, as desired to provide a suitable second membrane 14. The mean pore size may be in the range of 5 nm to 200 nm, alternatively in the range of 10 nm to 100 nm as determined by the Mean Pore Size Test Method specified herein.

Specifically, the mean pore size of the second membrane 14 may be configured to provide a consistent scent profile. Membrane Technology and Applications, 3rd Edition by Richard W. Baker (ISBN: 978-0-470-74372-0), pages 79 to 86 describe that the gas transport mechanism of a microporous membrane depends on the mean pore size. Based on an assumption that vapors of the volatile material ("organic vapors") such as, for example, perfume raw materials ("PRMs"), behave substantially like gases, a vapor transport mechanism of the second membrane 14 in the apparatus 1 similarly depend on a mean pore size of the second membrane 14.

The second membrane 14 may comprise a mean pore size >2λ, wherein λ is a mean free path of vapor of a volatile compound in the volatile material. It is believed that vapor transport through the second membrane 14 may take place by Poiseuille flow. When the pore size is so large that Poiseuille flow dominates, the second membrane 14 predominantly functions to reduce a vapor release rate of the volatile material.

Alternatively, the mean pore size of the second membrane 14 may be configured to be selective, i.e. control flow of vapor PRMs, i.e. vapor 12B present in the vapor chamber 15 and thereby controlling a scent profile of the volatile material 12 as described below. For example, the second membrane 14 may comprise a mean pore size <2λ. In such configurations, it is believed that vapor transport may take place through the second membrane 14 as defined by Knudsen flow. When Knudsen flow dominates, the vapor 12B across the second membrane 14 may be proportional to $1/\sqrt{M}$ where M is the molecular weight of the permeating molecule. The selectivity of the second membrane 14 for component i to component j is defined by Formula (2):

$$\sqrt{M_j}/\sqrt{M_i} \qquad (2),$$

wherein Mj, Mi corresponds to molecular weights of component j and component i respectively.

In this scenario, the second membrane 14 may regulate the transport of vapor PRM by facilitating the transport of PRM molecules with smaller molecular weights. A person skilled in the art would appreciate that molecular weight as used herein refers to the mass of the PRM molecule which can be calculated based on defining the specific PRM. In general, the molecular weights of the most volatile PRMs are typically lower than molecular weights of the least volatile PRMS, but exceptions are present. For example, wherein the volatile material 12 comprises a mixture of PRMs, the molecular weights of the PRMs generally range from 100 to 300 g/mol. Taking the lower and upper limits of molecular weights, the selectivity of the second membrane 14 is about 1.7 which is calculated based on Sample Calculation 1 as shown below:

$$\sqrt{(300)}/\sqrt{(100)}=1.7 \qquad \text{(Sample Calculation 1)}$$

Specifically, as the mean pore size becomes smaller, adsorption and capillary condensation occurs. In the context of gas transport, the higher the critical temperature of a gas, the more condensable. Highly condensable gas molecules are more likely to condense in the pores. In a multicomponent gas mixture, pore blockage occurs and the transport of the more condensable gas is favored over the less condensable gas. Similarly, in a vapor PRM mixture, transport of the least volatile PRM is favored over the most volatile PRM. This is shown by Formula (3) below which is presented in Uhlhorn R. J. R, Keizer K., Burggraaf A. J., Gas Transport and separation with ceramic membranes, Part I. Multilayer diffusion and capillary condensation, J. Membr. Sci. 66 (1992) 259-269.

$$\frac{\rho RT}{M}\ln\left(\frac{P_t}{P_o}\right) = -\frac{2\sigma\cos\theta}{r}, \qquad (3)$$

where ρ is the density of the condensate, R is the ideal gas constant, T is the temperature, M is the molecular weight, σ is the interfacial tension, θ is the contact angle, r is the pore radius, $P_o$ is the saturation vapor pressure and $P_t$ is the capillary condensation pressure.

Rearrangement of Formula (3) show that $P_t$ directly proportional to $P_o$. For a low volatile PRM (i.e. small $P_o$), the capillary condensation pressure is lower which means the low volatile PRM condenses more easily in the pores. This is a benefit for perfume transport using microporous membranes. Perfume delivery of the current single-membrane configuration is dependent only on the perfume vapor pressures (i.e. top notes evaporate very fast and does not last till end-of-life). Capillary condensation and pore blockage suppress transport of more volatile components and facilitates transport of less volatile components. The second membrane 14 can potentially be selective for less volatile components over more volatile components. It will be appreciated that for gas separation, capillary condensation occurs when pore size is 5 to 10 nm. Accordingly, as organic vapors are highly condensable chemical species, capillary condensation is likely to occur in pore size larger than 10 nm and thereby providing the benefit of controlling perfume transport based on a desired scent character profile.

The mean pore size may be substantially the same as the molecule kinetic diameter, such as for example, the mean pore size may be in the range of 0.5 to 1 nm. It will be appreciated that molecular sieving occurs when the pore diameter is similar to the molecule kinetic diameter. Molecules with kinetic diameter smaller than the mean pore size can pass through the second membrane 14 and molecules with kinetic diameter larger than the mean pore size cannot. Further, the second membrane 14 may be non-porous and for a non-porous membrane, solution-diffusion dominates. The membrane selectivity is a product of diffusivity selectivity and solubility selectivity. Diffusivity selectivity is largely due to differences in molecular dimensions. Solubility selectivity is due to affinity between the permeating molecules and the membrane material. For a mixture of vapor PRMs, the second membrane 14 is solubility-selective. If a top note has lower affinity to the membrane than a bottom note, and the membrane is solubility selective, it may facilitate transport of the bottom note.

Referring to FIG. 2, the second membrane 14 may be attached to an outer periphery 19 of the container 10 such that at least a portion of the second membrane 14 encloses the container 10. However, it should be appreciated that the first and second membranes 13, 14 may be arranged in any way as long as the vapor chamber 15 defines a space between the first and second membranes 13, 14 which prevents direct contact between the at least a portion of first membrane 13 and at least a portion of the second membrane 14.

The vapor chamber 15 is designed to minimize wetting of the second membrane 14 and enables delivery of the volatile material 12 from the apparatus 1 to be primarily by means of diffusion of vapor of the volatile material 12 versus being solely dependent on vapor pressures of volatile components in the volatile material 12.

Method

To explain the way the vapor chamber 15 and the second membrane 14 works to provide the reduced vapor release rate of the volatile material 12 according to the present invention, it is helpful to understand how a vapor release rate of the volatile material 12 is generated. A method of delivering a volatile material 12 according to the present invention is described with reference to FIGS. 3A, 3B and 3C which are schematic drawings illustrating the movement of a liquid phase 12A and/or a vapor phase of the volatile material 12 ("vapor 12B") across the first and second membranes 13, 14 respectively over time. The volatile material 12 may be comprised in an apparatus 1 as shown in the above figures according to the present invention. For illustrative purposes, the volatile material 12 may be described as a liquid perfume comprising a mixture of perfume compounds including but not limited to ethyl-2-methyl butyrate, benzyl acetate, phenyl ethyl alcohol and cyclamen aldehyde. Table 1 below shows each perfume compound in an amount of 25% by weight of the liquid perfume and lists their physiochemical parameters including molecular structure, molecular weight, boiling point, vapor pressure, and solubility parameter. The perfume compounds below are commercially available from Sigma Aldrich and the physiochemical properties were obtained from Aspen Properties® V9 database. However, it will be appreciated that any volatile material capable of transitioning from a solid and/or liquid phase to a vapor phase may be employed.

TABLE 1

| Chemical name | Molecular structure | Molecular weight, (g/mol) | Boiling point, (° C.) | Vapor pressure at 25° C. (kPa) | Solubility parameter *, (Joul/cm$^3$)$^{0.5}$ | Conc. in model perfume solution, (wt %) |
|---|---|---|---|---|---|---|
| Ethyl-2-methyl butyrate | C$_7$H$_{14}$O$_2$ | 130.20 | 132-133 | 1.25 | 16.6 | 25 |
| Benzyl acetate | C$_9$H$_{10}$O$_2$ | 150.18 | 212 | 0.0211 | 19.9 | 25 |
| Phenyl ethyl alcohol | C$_8$H$_{10}$O | 122.17 | 219-221 | 0.0116 | 22.0 | 25 |
| Cyclamen aldehyde | C$_{13}$H$_{18}$O | 190.30 | 270 | 0.00676 | 18.9 | 25 |

* The solubility parameter is calculated according to the Hildebrand equation.

Figures 3A, 3B, 3C:
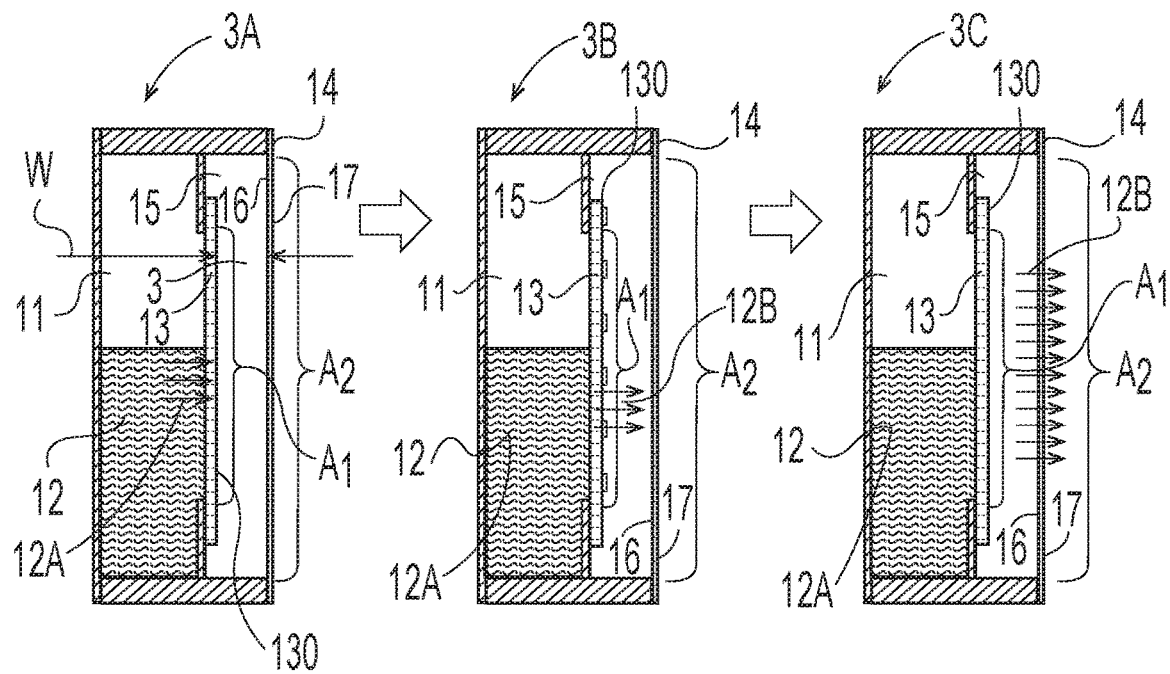
FIG. 3A to 3C are schematic drawings which show the movement of a liquid or vapor phase of a volatile material across the membranes in an apparatus for delivering a volatile material according to the invention.
Figures 4A, 4B, 4C:
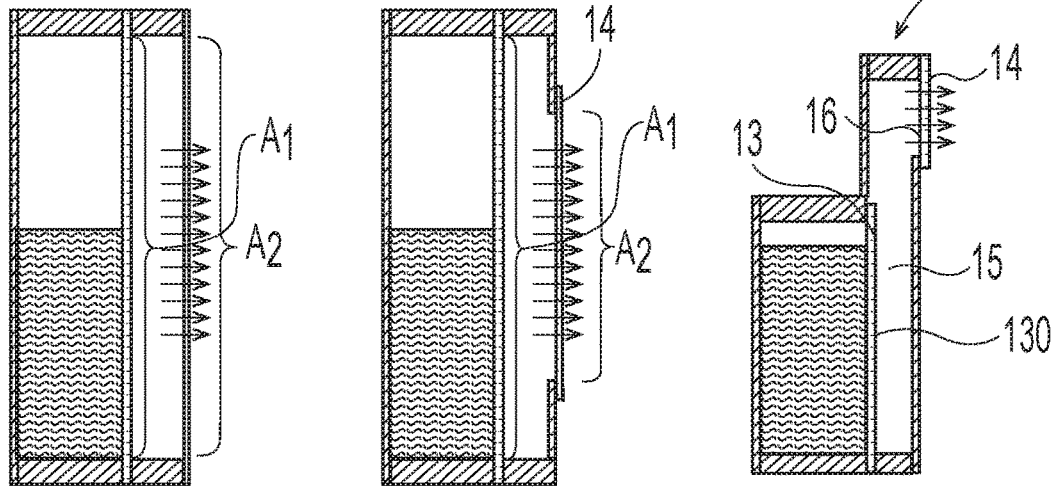
FIGS. 4A to 4C are schematic drawings which show different configurations of the membranes in an apparatus for delivering a volatile material according to the present invention.

In FIGS. 3A, 3B and 3C, the apparatus 1 is in a substantially vertical orientation. The container 10 is partially filled with the volatile material 12. The volatile material 12 includes volatile components comprising molecules such as for example, perfume molecules. FIG. 3A illustrates a first step 3A of the method in which the liquid phase 12A of the volatile material 12 passes through the first membrane 13 and/or a vapor 12B of the volatile material 12B passes through a non-wetted portion of the first membrane. FIG. 3B illustrates a second step 3B of the method in which the vapor 12B of the volatile material 12 is formed in the vapor chamber 15 and FIG. 3C illustrates a third step 3C of the method in which the vapor 12B passes through the second membrane 14 into the atmosphere.

Referring to FIG. 3A, the reservoir 11 comprises the liquid phase 12A of the volatile material 12 wherein molecules in the liquid phase 12A move through the first membrane 13 until a sufficiently high level of molecules is absorbed within the first membrane 13. The liquid phase 12A of the volatile material 12 may wet the first membrane 13 by means of capillary flow of the volatile material 12 into pores of the first membrane 13. Once the first membrane 13 is wetted, the liquid phase 12A of the volatile material 12 is disposed near or at the inner surface 130 of the first membrane 13 such that molecules near surface 130 of the first membrane 13 have enough kinetic energy to evaporate from the surface 130 and turn into a vapor phase of the volatile material 12 ("vaporization") and form a vapor 12B in the vapor chamber 15 as shown in FIG. 3B.

The vapor chamber 15 separates the liquid phase 12A of the volatile material 12 from the second membrane 14, thereby minimizing wetting of the second membrane 14 by the liquid phase 12A. Referring to FIG. 3B, the second membrane 14 comprises a first surface 16 facing the vapor chamber 15 (hereinafter "inner surface 16 of the second membrane 14") and a second surface 17 facing away from the vapor chamber 15 (hereinafter "outer surface 17 of the second membrane 14"). Once in the vapor chamber 15, the concentration level of molecules in the vapor 12B may increase to a level such that the molecules can diffuse out of the second membrane 14 through the outer surface 17 of the second membrane 14 into the surrounding atmosphere (outside of the apparatus 1 as shown in FIG. 3C) because of the atmosphere having a lower concentration of the molecules of the volatile material 12 than exists in the vapor chamber 15. Specifically, the vapor release rate of the vapor 12B into the atmosphere at a given time depends on the physico-chemical properties of the second membrane 14, and consequently the vapor release rate of the apparatus 1 is no longer only dependent on individual vapor pressures of the volatile components of the volatile material 12. Consequently, the present invention achieves a reduced initial release rate of the volatile material 12 as described in Example II.

Figure 30:
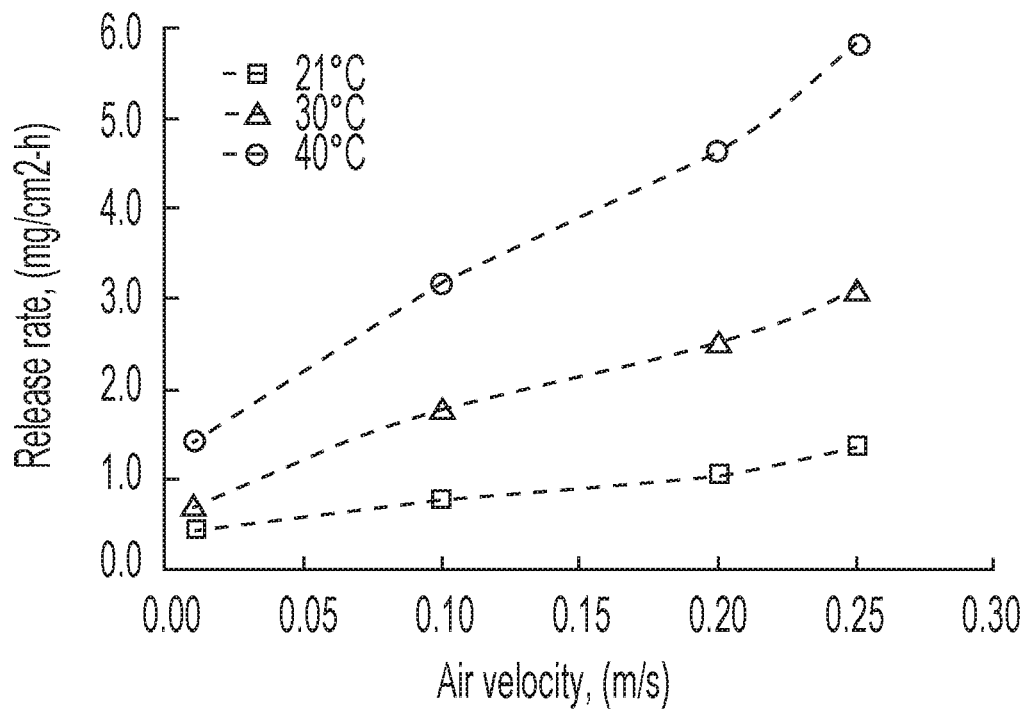
FIG. 30 is a graph plotting vapor release rates of one of the volatile materials (benzyl acetate) released from Comparative Sample A as a function of air velocity.
Figure 31:
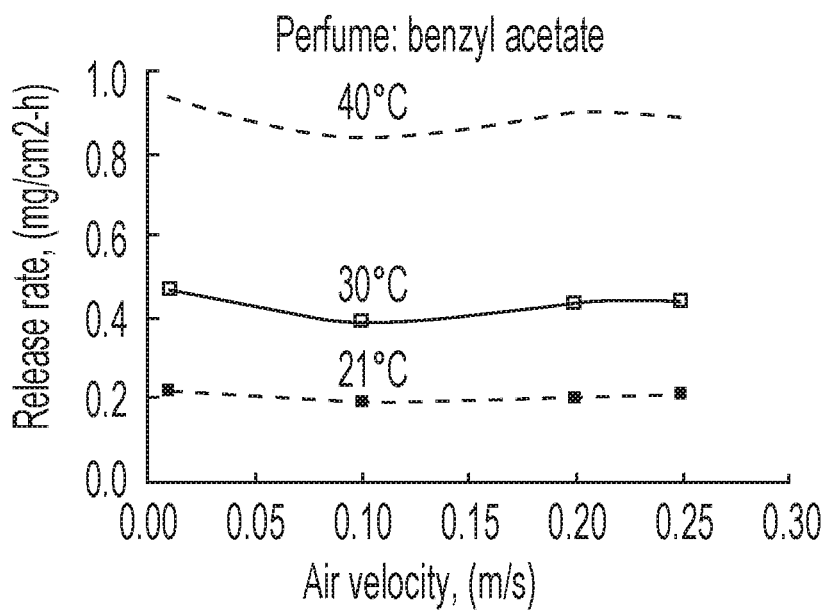
FIG. 31 is a graph plotting vapor release rates of one of the volatile materials (benzyl acetate) released from Inventive Sample O as a function of air velocity.

Further, having the second membrane 14 between the vapor chamber 15 and the atmosphere enable reducing temperature and/or air flow effects from the atmosphere on the volatile components of the volatile material 12 and the results are shown in Example VII with reference to FIG. 30 and FIG. 31.

The above described method of the present invention can be used to deliver volatile materials in a substantially continuous manner. Further, the method may allow for the delivery of volatile materials with improved uniformity of intensity throughout the duration of the intended use of the apparatus 1. The continuous emission of the volatile materials can be of any desired length of time, including but not limited to, up to: 20 days, 30 days, 60 days, 90 days, shorter or longer periods, or any period between 30 to 90 days.

The method of the present invention is suitable for purposes of providing fragrances, air fresheners, deodorizers, odor eliminators, malodor counteractants, insecticides, insect repellants, medicinal substances, disinfectants, sanitizers, mood enhancers, and aromatherapy aids, or for any other purpose using a material that acts to condition, modify, or otherwise change the atmosphere or the environment.

Further, referring to FIG. 3A, the vapor chamber 15 may comprise a gap 3 for receiving the vapor. The size of the gap 3 may be uniform and constant along the longitudinal direction (length) of the second membrane 14. Specifically, the gap 3 may comprise a width (W) (as shown in FIG. 3A) between surface 130 of the first membrane 13 facing the vapor chamber 15 and the inner surface 16 of the second membrane 14.

The width (W) of the gap 3 may influence the time it takes before the vapor of the volatile material 12 is released into the atmosphere. Specifically, in general, the larger the width (W) of the gap 3, the longer it may take for the vapor of the volatile material 12 to pass through both the first membrane 13 and the second membrane 14. Thus, the performance of the apparatus 1 can be adjusted by the manufacturer, and possibly even the user, by configuring the width (W) between the first membrane 13 and the second membrane 14. Although the width (W) of the gap can be any dimension suitable for the particular application, it has been found that a width (W) of the gap 3 in the range of 0.01 mm to 12 mm, preferably in the range of 4 mm to 12 mm and is preferably at least 0.5 mm, more preferably at least 2 mm or even more preferably at least 4 mm generally works well for disposable air freshener products such as the one shown in FIG. 1. However, the width (W) of the gap 3 may be increased or decreased according to meet the desired attributes for the particular device.

Specifically, the gap 3 between the first membrane 13 and the second membrane 14 creates a boundary layer, i.e. a layer of stationary fluid, on the outer surface 130 of the first membrane 13, which reduces the overall vapor release rate of volatile material 12 from the apparatus 1. The results are demonstrated in Example VI.

Figure 10A:
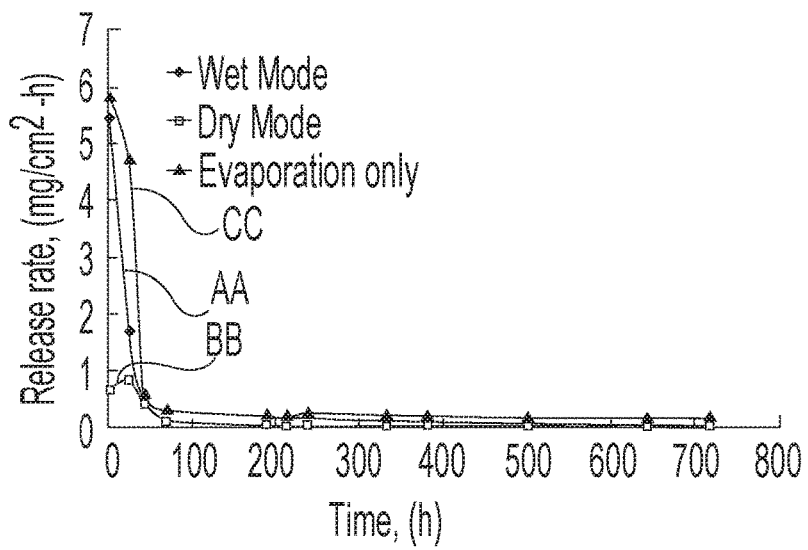
FIG. 10A is a graph plotting vapor release rates of volatile materials released from Comparative Samples A, B and C respectively as a function of time.

Referring to FIGS. 3A, 4A, 4B and 4C, the second membrane 14 may comprises a vapor surface area A2 (hereinafter "surface area A2") configured to allow the vapor 12B to pass through the second membrane 14 at a vapor release rate of greater than or equal to 0.06 mg/cm2-h and less than 4 mg/cm2-h at an air velocity of 0.1 m/s and a temperature of 25° C. A release rate of the above range is less than a release rate of a conventional air freshener (Comparative Sample A) in an initial time period as shown in FIG. 10A.

Referring to FIG. 3A, the surface area A2 of the second membrane 14 may be larger than a surface area A1 of the first membrane 13 so as to help facilitate attachment of the second membrane 14 to the periphery 19 of the container 10, especially when using conventional adhesive and heat sealing manufacturing processes and methods. Alternatively, referring to FIG. 4A, the surface area A2 of the second membrane 14 may be equal to than the surface area A1 of the first membrane 13. Further, referring to FIG. 4B, the surface area A2 of the second membrane 14 may be less than the surface area A1 of the first membrane 13.

Although the specific size of the membranes may vary depending on the specific apparatus and intended use, for typical size household air fresheners, the surface area A1 of the first membrane 13 and/or the surface area A2 of the second membrane 14 may be about 2 cm$^2$ to about 100 cm$^2$, about 2 cm2 to about 25 cm$^2$, about 10 cm$^2$ to about 50 cm$^2$, about 10 cm$^2$ to about 45 cm$^2$, about 10 cm$^2$ to about 35 cm$^2$, about 15 cm$^2$ to about 40 cm$^2$, about 15 cm$^2$ to about 35 cm$^2$, about 20 cm$^2$ to about 35 cm$^2$, about 30 cm$^2$ to about 35 cm$^2$, or about 35 cm$^2$.

In the above figures, such as in FIG. 3A, at least a part of the surface 130 of the first membrane 13 may be arranged to be opposite to the inner surface 16 of the second membrane 14. However, referring to FIG. 4C, it will be appreciated that the at least a part of the surface 130 of the first membrane 13 may be offset from the inner surface 16 as long as there is a vapor chamber 15 disposed between the first and second membranes 13 and 14. The first membrane 13 and/or the second membrane 14 may comprise the same or different material(s), details of which are described below.

Vapor Impermeable Substrate

Referring to FIGS. 5, 6 and 7, apparatus 1 may further include a vapor impermeable substrate 40 adjacent to the first membrane 13 or the second membrane 14, wherein the vapor impermeable substrate 40 is configured to prevent release of the volatile material 12 before use. Referring to FIG. 5, the vapor impermeable substrate 40 may be disposed adjacent to the second membrane 14. For example, the vapor impermeable substrate 40 may be releasably attached to the second surface 17 of the second membrane 14 to form a removeable cover for the apparatus 1. The vapor impermeable substrate 40 may be rupturable to allow the volatile material 12 to pass through when ruptured. For example, as shown in FIG. 6, the vapor impermeable substrate 40 may be a rupturable substrate disposed adjacent to the first membrane 13 and attached to an inner periphery 18 of the container 10 to form a sealed reservoir adjacent the first membrane 13.

The vapor impermeable substrate 40 may be made of any material that can be ruptured with a pre-determined applied force, with or without the presence of an element, such as rupture element 50, to aid in such rupture. In embodiments where the vapor impermeable substrate 40 is intended to contain the volatile material 12 when the apparatus 1 is not in use, the vapor impermeable substrate 40 may be made from any suitable barrier material that reduces or prevents evaporation of the volatile material 12. Such materials may be impermeable to vapors and liquids. Suitable barrier materials for the vapor impermeable substrate 40 include, but are not limited to coated or uncoated films, such as polymeric films, webs, foils, and composite materials such as foil/polymeric film laminates. An example of a foil that may be used as a barrier material is a 20 micron aluminum foil including a nitrocellulose protective lacquer, a polyurethane primer, and a 15 g/m2 polyethylene coating (Lidfoil 118-0092), available from Alcan Packaging. Suitable polymeric films include, but are not limited to, polyethylene terephtalate (PET) films, acrylonitrile copolymer barrier films such as, for example, those sold under the tradename Barex® by INOES, ethylene vinyl alcohol films, and combinations thereof. It is also contemplated that coated barrier films may be utilized as the vapor impermeable substrate 40. Such coated barrier films include, but are not limited to, metallized PET, metalized polypropylene, silica or alumina coated film.

Referring to FIG. 6, rupture element 50 may be integrally formed with apparatus 1 such as with the end wall 120 of the apparatus 1 such that a user can activate the rupture element 50 and puncture the vapor impermeable substrate 40. For example, the user may activate the rupture element 50 by pressing a pre-determined portion of the apparatus 1 just prior to using the device. The rupture element 50 may integrally formed with a portion of the apparatus 1 or may be joined to a portion thereof. Alternatively, as shown in FIG. 7, the rupture element 50 may be integrally formed with or joined to a rupture frame 51 disposed within the apparatus 1.

Volatile Material

The volatile material 12 may comprise one or more perfume compounds, or a mixture of perfume compounds. The volatile material 12 can be in the form of perfume oil and can include one or more essential oils, volatile organic compounds, or mixtures thereof. Furthermore, the volatile material 12 can include synthetically or naturally formed materials. Examples include, but are not limited to: oil of bergamot, bitter orange, lemon, mandarin, caraway, cedar leaf, clove leaf, cedar wood, geranium, lavender, orange, origanum, petitgrain, white cedar, patchouli, neroili, rose absolute, and the like.

The volatile material 12 may alternatively be in the form of a crystalline solid, which has the ability to sublime into the vapor phase at ambient temperatures or be used to fragrance a liquid. Any suitable crystalline solid in any suitable amount or form may be used. For example, suitable crystalline solids include but are not limited to: vanillin, ethyl vanillin, coumarin, tonalid, calone, heliotropene, musk xylol, cedrol, musk ketone benzohenone, raspberry ketone, methyl naphthyl ketone beta, phenyl ethyl salicylate, veltol, maltol, maple lactone, proeugenol acetate, evemyl, and the like.

In the case of air freshener or fragrances, different volatile materials can be used together that are similar, related, complementary, and/or contrasting. In addition to volatile materials, the apparatus 1 may include any known compounds configured to neutralize odors.

The following examples are intended to more fully illustrate the present invention and are not to be construed as limitations of the present invention since many variations thereof are possible without departing from the scope of the present invention. All parts, percentages and ratios used herein are expressed as percent weight unless otherwise specified.

Test Equipment/Materials

Equipment and materials used for each of the Examples set forth herein are listed in Table 2 below. FIG. 8 shows a lab-built air freshener testing system 70 for measuring vapor release rate as a function of air velocity and/or temperature. The system 70 has an air chamber 71 for receiving vapor of a volatile material being tested. The air chamber 71 includes a mass flow controller 72 for measuring flow rate of air within the chamber 71, a heat exchanger 73 for heating or cooling of the air, and a thermal controller 74 for controlling the temperature in the chamber. Comparative and Inventive Samples used for testing in the Examples are described under the respective Examples.

TABLE 2

| Equipment/Materials | Technical Specifications |
|---|---|
| Air Chamber 71 | Dimensions = 6 × 10 × 59 cm |
| | Material = Aluminum and Poly(methyl methacrylate) |
| | Air temperature: 21-40° C., |
| | Air velocity: 0.01-0.25 m/s |
| | Relative Humidity: <5% |
| Mass flow controller 72 | Supplier Name: Bronkhorst |
| | Model/Serial No.: F-202AV DMFC |
| Heat exchanger 73 | Supplier Name: CELLNERGY ENGINEERING PTE LTD |
| | Model/Serial No.: Customized/N/A |
| Thermal controller 74 | Supplier Name: Delta |
| | Model/Serial No.: DTB4848 |
| Fume Hood | Supplier Name: Eltron Engineering Pte Ltd. |
| | Model: Rectangle hood |
| | Air temperature: approximately 25° C. |
| | Air velocity: approximately 0.1 m/s |
| | Relative Humidity: 60% |
| Balance for Weight Measurement | Supplier Name: Denver Instrument |
| | Model/Serial No.: TB214 |
| Flame ionized detector (FID) | Supplier Name: Agilent |
| | Model/Serial No.: G3461-64000 |
| Capillary Flow Porometer | Supplier Name: PorousMaterialsInc.,USA |
| | Model/Serial No.: CFP-1500AE |

Test Methods/Calculation(S)

Vapor Release Rate Test Method (Chamber Method)

Each of the Comparative and Inventive Samples described in Example VII is weighed ($W_1$) with a Denver Instrument balance and placed in a predetermined location inside the chamber 71. The predetermined location, air velocity, flow pattern, and air temperature (air relative humidity <5%) are the same for all of the Samples. Specifically, the air velocity in the chamber 71 is 0.1 m/s unless otherwise specified and the air temperature in the chamber 71 was 25° C. The system 70 is stabilized for 2 hours before each sample was weighed ($W_2$) again to obtain a perfume release rate. The samples are conditioned for a minimum time of 2 hours to remove moisture from the samples before testing. After measuring W1 and W2, the vapor release rate is determined based on Formula (4):

$$\text{Release rate} = \frac{W_1 - W_2}{A(t_2 - t_1)} \quad (4)$$

wherein,
A=vapor surface area of the second membrane
$t_1$=a first time period after activation
$t_2$=a second time period after activation
$W_1$=weight of the dispenser at $t_1$
$W_2$=weight of the dispenser at $t_2$.

Vapor Release Rate Test Method (Hood Method)

The vapor release rates of the samples are determined as described for the Vapor Release Rate Test Method (Chamber) but test conditions and placement of the samples differ from the Vapor Release Rate Test Method as follows: the samples are tested in a fume hood in an air-conditioned room.

Vapor Release Rate Test Method (Room)

The vapor release rates of the samples are determined as described for the Vapor Release Rate Test Method (Chamber) but test conditions and placement of the samples differ as follows: The samples are placed in a 2.0 m×3.4 m×2.8 m room. The conditions of the room are:
Air velocity—10 air changes per hour (velocity ~0.1 m/s),
Air Temperature—21 deg C.
Relative Humidity—40% RH.

Mean Thickness Test Method

A mean thickness of the membrane is measured using a Mitutoyo micrometer (model: ID-C112MXB).

Air Gap Measurement Method

The air gap between the first membrane and the second membrane of each of the relevant Samples is measured using a Mitutoyo caliper (model: CD-6" CS).

Mean Pore Size Test Method

The mean pore size of the pores of the membranes is measured by a CFP-1500AE capillary flow porometer (Porous Materials Inc., USA). A PMI Galwick solution with a surface tension of 15.9 dynes/cm is used to wet the membranes. A piece of membrane is immersed in the Galwick solution for 1 day to ensure complete wetting of the membrane before mounting it into a chamber in the porometer. Then the nitrogen gas is allowed to flow into the chamber gradually. The mean pore size is calculated at the flow pressure corresponding to the intersection of the wet flow curve and the half-dry flow curve which was the half of the flow rate through the dry membrane (dry flow curve). The definitions of wet flow curve and half-dry flow curve may be presented in such as for example in "A. Jena, K. Gupta, Flow Porometry: What can Flow porometry do for us? Porous-Materials, Inc., Ithaca, N.Y., USA, 2002.". The pore diameter data are computed by the supplier-provided software that comes with CFP-1500AE capillary flow porometer, i.e., PMI software, after testing.

Gas Chromatography ("GC") Test Method

The concentrations of the perfume compounds in the perfume reservoir are measured by using a Hewlett-Packard GC7890 with a flame ionized detector (FID) for measuring concentration of organic species in a gas stream. Before injection, the perfume samples from the reservoir are diluted with ethanol (i.e. 1 g of sample to 99 g ethanol). The samples are injected in an apolar column (MEGA-5MS, 50 m×0.25 mm×0.25 μm). The temperature in the oven is held at 50° C. for the first 3.5 minutes, increased to 100° C. at a rate of 10° C. per minute, then further increased to 240° C. at a rate of 30° C. per min and held for 3 min. A splitless mode is used; 1 μL of the sample is injected and the inlet temperature was 250° C. The concentration is determined by an External Calibration Curve Method which is a method for determining the concentration of a substance in an unknown sample by comparing the unknown sample to a set of standard samples of known concentration. The External Calibration Curve Method is known to the person skilled in the art of gas chromatography and will not be further described.

Porosity Calculation Method

The membrane porosity, ε, is calculated according to Formula (5) below.

$$\varepsilon = \frac{\rho_{mat} - \rho_{mem}}{\rho_{mat}} \times 100\% \quad (5)$$

where $\rho_{mem}$ is the membrane density, which is equal to the membrane weight in air divided by its volume. The density of the membrane material, $\rho_{mat}$, was estimated using a Mettler Toledo analytical balance ML204 and a density kit ML-DNY-43 (Zurich, Switzerland). The density kit applied the Archimedes' principle based on Formula (6) and the measured membrane weights in air and liquid.

$$\rho_{mat} = \frac{M_{air}}{M_{air} - M_{liq}} \rho_{liq} \quad (6)$$

where $\rho_{liq}$ is the density of the applied liquid (i.e., hexane). $M_{air}$ and $M_{liq}$ refer to the membrane weights in air and liquid, respectively.

Pore Size Calculation Method

Pore size of a membrane is obtained based on the following calculation. Ethyl-2-methyl butyrate in a vapor form may comprise a mean free path (λ) which is determined to be $$36.5 \text{ nm} \left[ \frac{1.38 \times 10^{-23} \times 298}{1.414 \times 3.14 \times (5.0 \times 10^{-10})^2 * 101325} = 36.5 \times 10^{-8} \text{m} \right]$$

based on Formula (1) described hereinbefore and provided below for easy reference.

$$\lambda = \frac{k_b T}{\sqrt{2} \pi d^2 P} \quad (1)$$

where $k_b$, the Boltzman constant, is $1.38 \times 10^{-23}$. P is the pressure in Pa and d is the kinetic diameter of the perfume vapor molecule that permeates the second membrane 14.

When the pore radius of the second membrane 14 is smaller than the mean free path of ethyl-2-methyl butyrate, vapor of ethyl-2-methyl butyrate passes through the second membrane 14 by Knudsen diffusion, the release rate of ethyl-2-methyl butyrate through the second membrane 14 may be calculated according to Knudsen flow equation below, Formula (7) which is presented in R. W. Schofield, A. G. Fane and C. J. D Fell, Gas and vapour transport through microporous membranes. I. Knudsen-Poiseuille transition, J. of Membr. Sci., 53 (1990) 159-171.

$$J_K = \frac{2}{3}\frac{r\varepsilon}{\chi}\left(\frac{8RT}{\pi M}\right)^{1/2}\frac{M}{RT}\frac{\Delta P}{\delta} \quad (7)$$

where r is pore radius, $\varepsilon$ is the membrane porosity, $\chi$ is the membrane tortuosity, M is the molecular weight, T is the temperature, R is the ideal gas constant, $\delta$ is the membrane thickness and $\Delta P$ is the pressure difference across the membrane.

For example, for a membrane comprising a membrane thickness of 100 μm, a tortuosity of 2 and a porosity of 50%, the pore radius may be less than 150 nm in order to reduce the release rate. A sample calculation based on Formula (7) is shown below to illustrate how the pore radius is derived Ethyl-2-methyl butyrate properties at 25° C.: P=1250 Pa, Mw=130.2 g/mol Membrane properties: $\varepsilon=0.5$, $\chi=2$, $\delta=1*10^{-4}$ m It is also known: $J_{ethyl\text{-}2\text{-}methyl\ butyrate}$=41.65 mg/cm²-h for Comparative Sample A such as shown in Example I described below.

Assuming downstream vapor pressure = 0 Pa $J_{ethyl\text{-}2\text{-}methyl\ butyrate}$ = 41.65 mg/cm² − h = 8.89 ∗ 10⁻⁴ mol/m² − s $$r = \frac{J_k}{\frac{2}{3}\frac{\varepsilon}{\chi}\left(\frac{8RT}{\pi \times M}\right)^{\frac{1}{2}}\frac{1}{RT}\frac{\Delta P}{\delta}}$$

$$= \frac{8.89\times 10^{-4}}{\frac{20.5}{32}\left(\frac{8\times 8.314\times 298}{3.14\times 130.2}\right)^{\frac{1}{2}}\frac{1}{8.314\times 298}\frac{1250}{1\times 10^{-4}}} =$$

$$1.517\times 10^{-7}\text{m} = 151.7\text{ nm}$$

In the above sample, the pore radius is 151.7 nm.

EXAMPLES

The following Examples were conducted according to the above described Test Methods/Theoretical Calculations to illustrate the embodiments of the present invention.

Example I

Figures 9A, 9B, 9C:
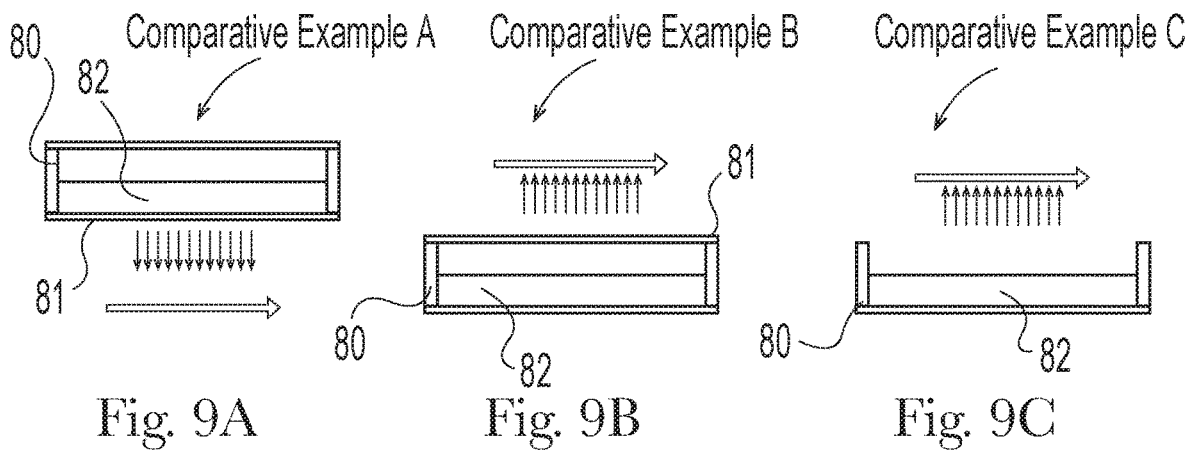
FIG. 9A is a schematic drawing of an air freshener having a membrane in contact with a volatile liquid ("Comparative Sample A")
FIG. 9B is a schematic drawing of an air freshener having a membrane not in contact with a volatile liquid ("Comparative Sample B")
FIG. 9C is a schematic drawing of an air freshener having a volatile liquid in an open container without a membrane ("Comparative Sample C")

The following samples in Table 3 are evaluated according to the Vapor Release Rate Test Method (Hood) described hereinbefore. This Example is to evaluate vapor release rates of a model perfume 82 (in a housing 80 comprising a single membrane 81 in a wet mode wherein the model perfume 82 is a liquid and the liquid is in contact with at least a part of the single membrane 81 (Comparative Sample A as shown in FIG. 9A), a housing 80 comprising a single membrane 81 in a dry mode (Comparative Sample B as shown in FIG. 9B), and a housing 80 without a membrane (Comparative Sample C as shown in FIG. 9C). Details of Comparative Samples A, B and C are set out in Table 3 below.

TABLE 3

| Parts/Parameters | Comparative Sample A | Comparative Sample B | Comparative Sample C |
|---|---|---|---|
| Weight of Model Perfume | 5 grams | 5 grams | 5 grams |
| Ingredients in Model Perfume | a) ethyl-2-methyl butyrate (25% by weight of the Model Perfume) b) benzyl acetate (25% by weight of the Model Perfume) c) phenyl ethyl alcohol (25% by weight of the Model Perfume) d) cyclamen aldehyde (25% by weight of the Model Perfume) | | |
| Container for Model Perfume | Size = Cylindrical with a diameter of 50 mm and a depth of 8 mm Material: Aluminum | | |
| First Membrane/Properties | Yes | Yes | None |
| a) Material | Polyethylene with silica | | N/A |
| b) Thickness (μm) | 279 | | N/A |
| c) Pore size (nm) | 20 nm | | N/A |
| d) Porosity (%) | 60 | | N/A |
| e) Membrane Surface Area | 19.63-cm² | | N/A |
| Membrane Wet/Dry Mode | Wet | Dry | N/A (Evaporation Mode) |

Table 4 show the vapor release rates of the Comparative Samples A, B and C as a function of time.

TABLE 4

| Comparative Sample | Time, h | 2.1 | 25.1 | 43.3 | 70.2 | 190.1 | 213.5 | 239.1 | 334.2 | 382.0 | 502.0 | 643.6 | 720.0 |
|---|---|---|---|---|---|---|---|---|---|---|---|---|---|
| A | Release rate (mg/cm²-h) | 5.44 | 1.70 | 0.42 | 0.29 | 0.23 | 0.17 | 0.14 | 0.12 | 0.09 | 0.07 | 0.05 | 0.04 |
| B | Release rate (mg/cm²-h) | 0.67 | 0.84 | 0.40 | 0.12 | 0.04 | 0.03 | 0.03 | 0.03 | 0.03 | 0.03 | 0.02 | 0.03 |
| C | Release rate (mg/cm²-h) | 5.82 | 4.70 | 0.57 | 0.29 | 0.20 | 0.18 | 0.23 | 0.20 | 0.18 | 0.16 | 0.15 | 0.17 |

Figure 10B:
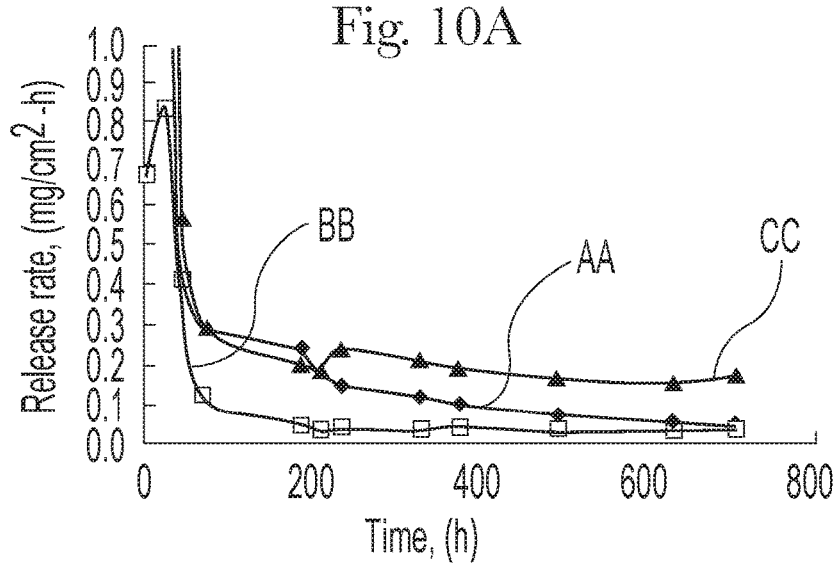
FIG. 10B is a detailed view of FIG. 10A.

FIG. 10A is a graph plotting vapor release rates of Comparative Samples A, B and C as a function of time. FIG. 10B is a portion of FIG. 10A expanded by a factor of 10 in the "Y" direction and reduced in the "X" direction to better show the vapor release rates of the Comparative Samples. Specifically, Profile AA on the graph represents Comparative Sample A and shows that the vapor release rate decreased from 6 to 0.03 mg/cm$^2$-h in the 720-hour test. Comparative Sample C, shown as Profile CC on the graph has a similar release rate to Profile AA. This is believed to be attributed to both examples having a vapor release rate that is primarily dependent on the vapor pressure of the perfume sample. On the other hand, Profile BB, corresponding to Comparative Sample B, has a vapor release rate of from 0.84 to 0.03 mg/cm$^2$-h in the 720-hour test. The difference in vapor release rates between Comparative Samples A and C, and B may be primarily attributed to the non-wetted boundary layer (in this case membrane 81) in Comparative Sample B created on the liquid-vapor interface of the housing 80, which provides some resistance to passage of the vapor through the membrane into the surrounding atmosphere as compared to wetted boundary layer of Comparative Sample A and the non-existent boundary layer of Comparative Sample C.

Comparative Samples D to I (in a similar configuration to Comparative Samples A and B) comprise pure perfume compounds and are prepared according to Table 5 below and are tested according to the Vapor Release Rate Test Method (Hood). As shown in Table 5, Comparative Sample D comprises ethyl-2-methyl butyrate in an amount of 100% by weight of a volatile material; Comparative Sample E comprises benzyl acetate in an amount of 100% by weight of a volatile material; Comparative Sample F comprises phenyl ethyl alcohol in an amount of 100% by weight of a volatile material.

TABLE 5

| Parts/Parameters | Comparative Sample | | | | | |
| --- | --- | --- | --- | --- | --- | --- |
| | D | E | F | G | H | I |
| Volatile Material Ingredients (wt %) | | | | | | |
| Ethyl-2-methyl butyrate | 100 | — | — | 100 | — | — |
| Benzyl Acetate | — | 100 | — | — | 100 | — |
| Phenyl Ethyl Alcohol | — | — | 100 | — | — | 100 |
| Container for Volatile Material | Size = Cylindrical with a diameter of 50 mm and a depth of 8 mm Material: Aluminum | | | | | |
| Membrane/Properties | | | | | | |
| a) Material | Polyethylene with silica | | | | | |
| b) Thickness (μm) | 279 μm | | | | | |
| c) Mean Pore size (nm) | 20 nm | | | | | |
| d) Porosity (%) | 60 | | | | | |
| e) Membrane Surface Area | 19.63-cm$^2$ | | | | | |
| Membrane Wet/Dry Mode | Dry | Dry | Dry | Wet | Wet | Wet |

Table 6 a summary comparing the vapor release rates of the perfume compounds of Comparative Samples D to I of Table 5.

TABLE 6

| Perfume compound | Vapor pressure at 25° C., (kPa) | Comparative Samples D, E, F dry mode release rate, (mg/cm$^2$-h) | Comparative Samples G, H, I wet mode release rate, (mg/cm$^2$-h) |
| --- | --- | --- | --- |
| Ethyl-2-methyl butyrate | 1.25 | 3.85 | 41.65 |
| Benzyl acetate | 0.0211 | 0.07 | 0.73 |
| Phenyl ethyl alcohol | 0.0116 | 0.0033 | 0.45 |

Referring to Table 7, when the membrane is in contact with the vapor phase of the perfume compound (ethyl-2-methy butyrate) only (Comparative Sample D), the vapor release rate of Comparative Sample D is 3.85 mg/cm²-h whereas when the membrane is in contact with the liquid phase of the perfume compound (ethyl-2-methyl butyrate) (Comparative Sample G), the vapor release rate of Comparative Sample G is higher relative to Comparative Sample D, i.e. 41.65 mg/cm²-h.

TABLE 7

| Comparative Sample | Release rate, (mg/cm²-h) |
|---|---|
| D | 3.85 |
| E | 0.07 |
| F | 0.0033 |
| G | 41.65 |
| H | 0.73 |
| I | 0.45 |

Example II

The following sample(s) are evaluated according to the Vapor Release Rate Test Method (Hood) and the GC Test Method described hereinbefore. Example II demonstrates that having a second membrane and a vapor chamber in an apparatus, such as apparatus 1 reduces the vapor release rate of a volatile material from the apparatus and delays the loss of high notes of a volatile material. Table 8 describes the configuration of samples used in Example II.

TABLE 8

| Parts/Parameters | Comparative Sample J | Inventive Sample A | |
|---|---|---|---|
| Model Perfume | 5 grams | 5 grams | |
| Ingredients in Model Perfume | a) ethyl-2-methyl butyrate (25% by weight of the Model Perfume) b) benzyl acetate (25% by weight of the Model Perfume) c) phenyl ethyl alcohol (25% by weight of the Model Perfume) d) cyclamen aldehyde (25% by weight of the Model Perfume) | | |
| Container for Model Perfume | Size = Cylindrical with a diameter of 50 mm and a depth of 8 mm Material: Aluminum | | |
| Membrane Properties | Single Membrane | First Membrane | Second Membrane |
| a) Material | | Polyethylene with silica | |
| b) Thickness (μm) | | 279 | |
| c) Pore size (nm) | | 20 | |
| d) Porosity (%) | | 60 | |
| e) Membrane Surface Area (cm²) | 19.63 (Based on a circular shape of the membrane with a 5 cm diameter. The surface area is 3.14*5²/4 = 19.625 cm².) | 19.63 (Based on a circular shape of the membrane with a 5 cm diameter. The surface area is 3.14*5²/4 = 19.625 cm².) | 19.63 (Based on a circular shape of the membrane with a 5 cm diameter. The surface area is 3.14*5²/4 = 19.625 cm².) |
| Membrane Wet/Dry Mode | Wet | Wet | Dry |

Figure 12:
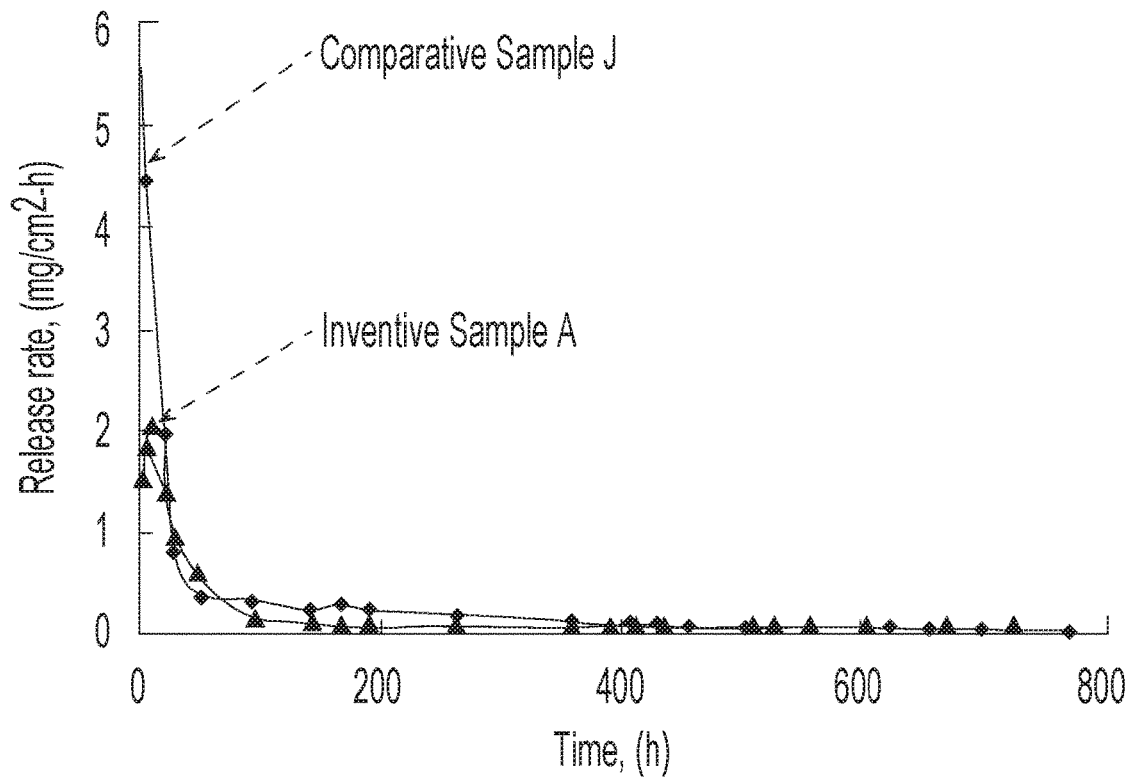
FIG. 12 is a corresponding graph of Table 9 plotting vapor release rates of volatile materials released from an apparatus for delivering a volatile material according to the present invention ("Inventive Sample A") as a function of time.

FIG. 11 illustrates Table 9 comprising the vapor release rates of Comparative Sample J and Inventive Sample A. FIG. 12 is the corresponding graphical plot of the vapor release rates of Comparative Sample J and Inventive Sample A as a function of time. A technical effect of having the second membrane 14 is that the vapor release rate of Inventive Sample A is lower relative to a vapor release rate of Comparative Sample J. The vapor release rate reduction is believed to be due to an increase of mass transport resistance from the second membrane 14.

Figure 13:
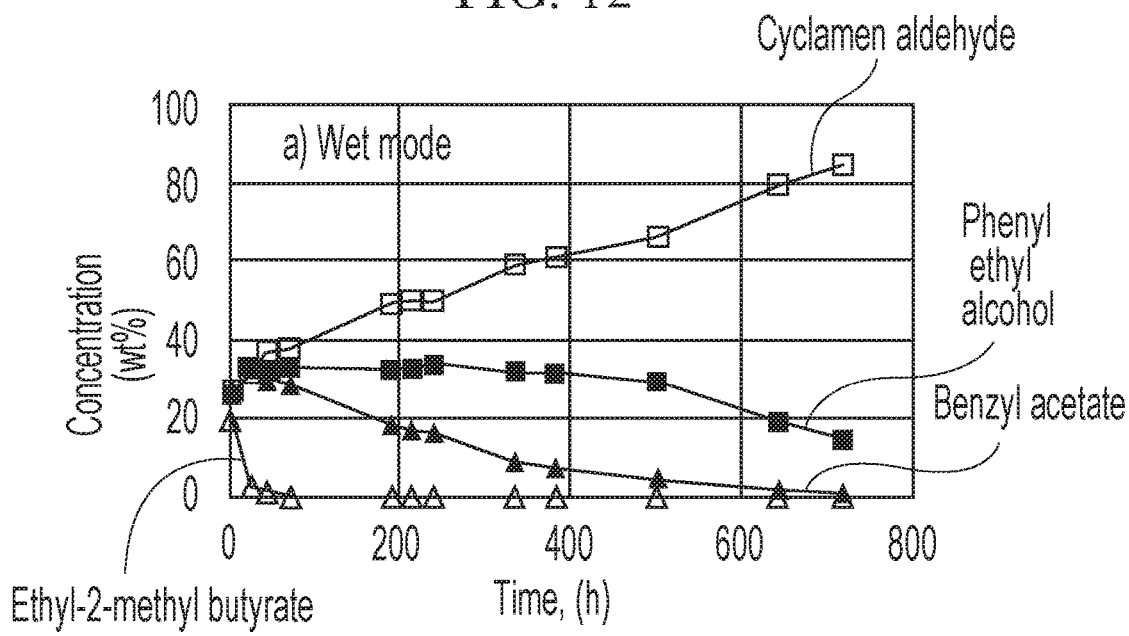
FIG. 13 is a graph plotting concentration (%) of volatile materials released from Comparative Sample A as a function of time.
Figures 14, 15:
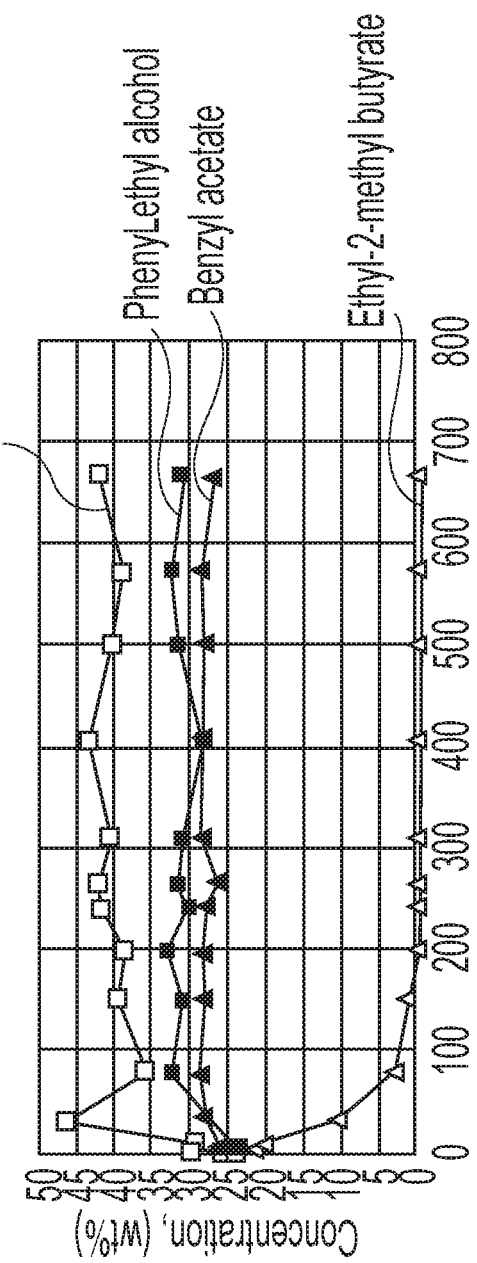
FIG. 14 illustrates Table 10 which reports concentrations (%) of volatile materials released from an apparatus for delivering a volatile material according to the present invention ("Inventive Sample A") as a function of time.
FIG. 15 is a corresponding graph of Table 10 plotting concentration (%) of volatile materials released from Inventive Sample A as a function of time.

The above samples are also evaluated according to the GC Test described hereinbefore. For FIG. 13 is a graph showing the concentration (wt %) of four perfume compounds (ethyl-2-methyl butyrate, benzyl acetate, phenyl ethyl alcohol, cyclamen aldehyde) included in perfume 82 over time when tested as set forth in Comparative Sample J. FIG. 14 illustrates Table 10 which shows the concentrations (wt %) of the same four perfume compounds (ethyl-2-methyl butyrate, benzyl acetate, phenyl ethyl alcohol, cyclamen aldehyde) of perfume 82 over time when tested as set forth in Inventive Sample A. FIG. 15 is the corresponding graphical plot.

Referring to FIGS. 14 and 15, for the configuration of Inventive Sample A, the concentration of ethyl-2-methyl butyrate drops to 0 wt % after approximately 100 hours while the concentration of benzyl acetate declines to 28.50 wt % after approximately 100 hours. These concentration drops of Inventive Sample A are significantly slower than the concentration drops of the same materials when tested in accordance with Comparative Sample J. Specifically, as shown in FIG. 13, the concentration of ethyl-2-methyl butyrate drops to 0% before 70 hours and the concentration of benzyl acetate reduces to 0.8 wt % at about 720 hours. These results provide an example showing how addition of a second membrane, as set forth in Inventive Sample A, can prolong the time for evaporating certain perfume ingredients, such as ethyl-2-methyl butyrate as compared to configurations where only a single membrane is provided. Slowing the vapor release rate, and thus retaining ethyl-2-methyl butyrate for a longer period of time can help enables a more consistent scent profile for the perfume over time and/or may extends the total time the perfume components remain volatile, which may be desirable in air freshening and other contexts. Accordingly, an air freshener product according to the present invention may have better product longevity relative to conventional air freshener products with a single membrane.

Example III

The following Samples are evaluated according to the Vapor Release Rate Test Method (Hood) and the GC Test described hereinbefore to demonstrate effect(s) of varying a mean pore size only in the second membrane. Table 11 describes the configuration of samples used in Example III.

TABLE 11

| Parts/Parameters | Inventive Sample B | Inventive Sample C | Inventive Sample D |
|---|---|---|---|
| Model Perfume similar to Model Perfume of Table 3 | 5 grams | 5 grams | 5 grams |
| Container for Model Perfume | Size = Cylindrical with a diameter of 50 mm and a depth of 8 mm Material: Aluminum | | |
| Membrane Properties | | | |
| First Membrane (Wet Mode) | Same properties as First Membrane of Inventive Sample A | | |
| Second Membrane (Dry Mode) | | | |
| a) Material | | Polyethylene | |
| b) Mean Thickness (μm) | 49 | 46 | 45 |
| c) Measured Mean Pore size (μm) (Pore Size from Supplier (nm) | 0.018 ± 0.012 (10 nm) | 0.074 ± 0.039 (100 nm) | 0.127 ± 0.060 (200 nm) |
| d) Porosity (%) | 67.1 | 59.2 | 64.9 |
| e) Membrane Surface Area (cm$^2$) | 19.63 (Based on a circular shape of the membrane with a 5 cm diameter. The surface area is 3.14*5$^2$/4 = 19.625 cm$^2$.) | 19.63 (Based on a circular shape of the membrane with a 5 cm diameter. The surface area is 3.14*5$^2$/4 = 19.625 cm$^2$.) | 19.63 (Based on a circular shape of the membrane with a 5 cm diameter. The surface area is 3.14*5$^2$/4 = 19.625 cm$^2$.) |

Figure 17:
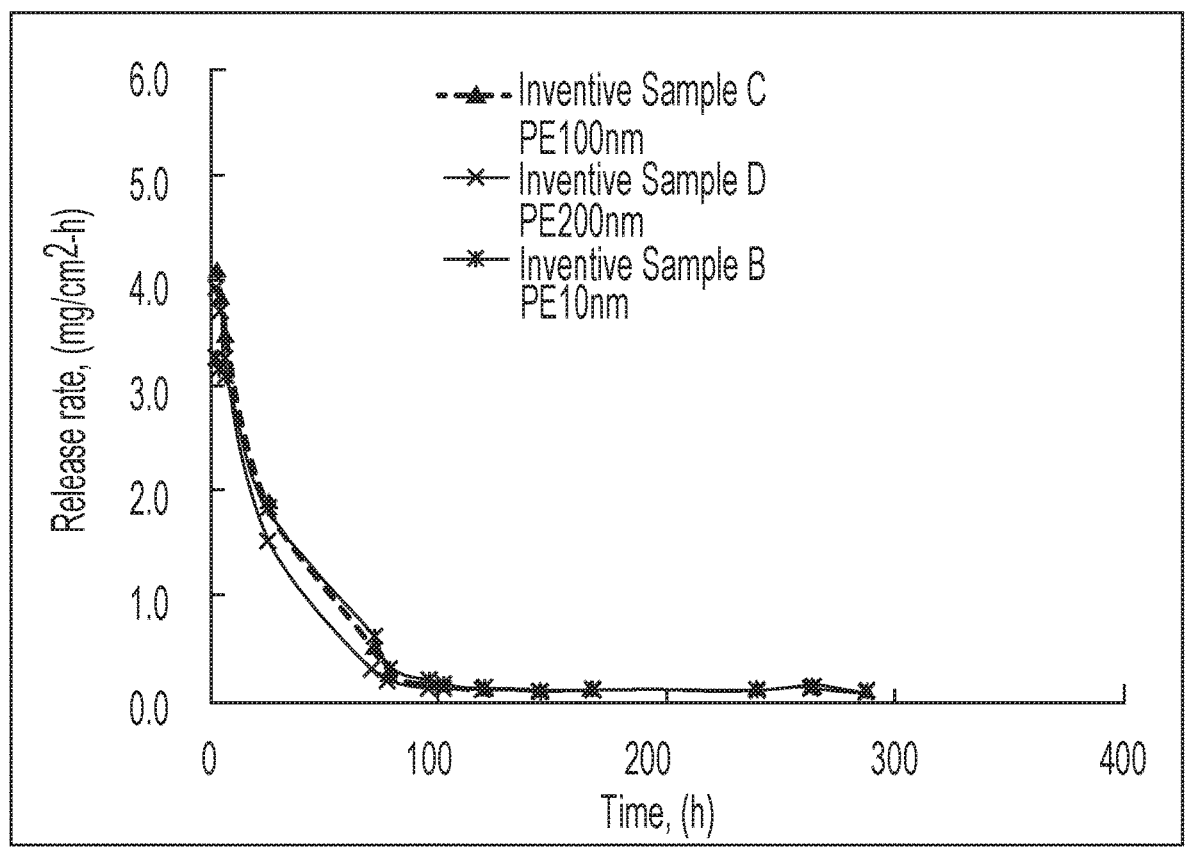
FIG. 17 is a corresponding graph of Table 12 plotting vapor release rates of volatile materials released from apparatuses with second membranes of different pore sizes according to the present invention ("Inventive Samples B, C, D") as a function of time.

FIG. 16 illustrates Table 12 which reports the vapor release rates of the above Inventive Samples B, C, D as a function of time. FIG. 17 is the corresponding graphical plot.

Referring to Table 12 and FIG. 17, the initial vapor release rates (up to 25 h) of Inventive Sample B are lower compared to vapor release rates of Inventive Sample C at the respective time because of the lower permeation rates of the most volatile compound, ethyl-2-methyl butyrate, through the second membrane 14. As time increases to 71.4 h, the vapor release rates of Inventive Sample B are higher compared to those of Inventive Sample C at the respective time because of the higher concentration of the more volatile compounds in the reservoir of Inventive Sample B. As the time increases to 144 h, the release rates are the almost same for Inventive Samples A and B when ethyl-2-methyl butyrate is depleted. Inventive Sample C has vapor release rates similar to Inventive Sample B. In view of the above, a smaller pore size of the second membrane may be desirable to prolong the longevity of high volatile compounds such as for example, ethyl-2-methyl butyrate.

Figures 18, 19:
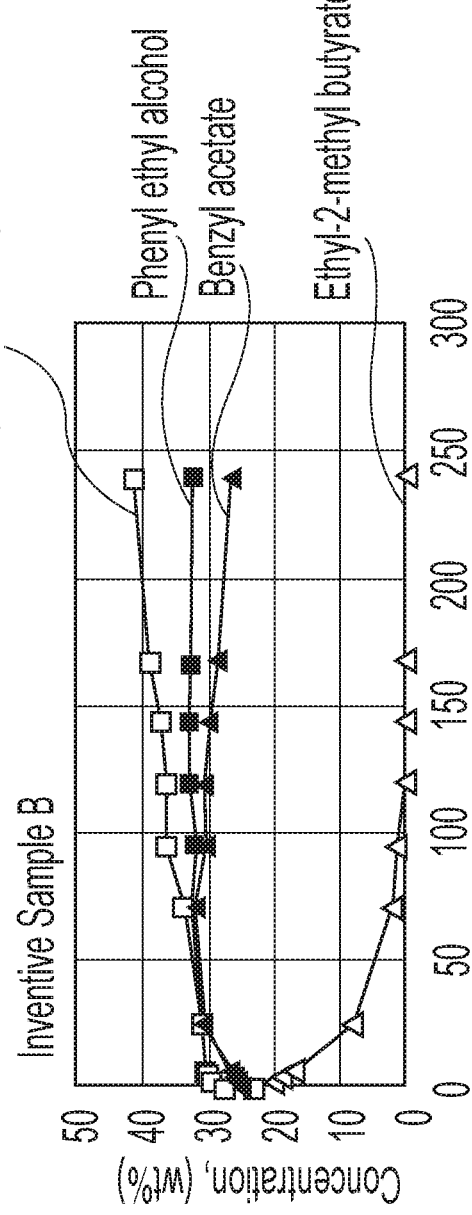
FIG. 18 illustrates Table 13 which reports concentrations (%) of volatile materials released from Inventive Sample B as a function of time.
FIG. 19 is a corresponding graph of Table 13 plotting concentration (wt %) of volatile materials released from Inventive Sample B as a function of time.

The above samples are also tested according to the GC Test described hereinbefore. FIG. 18 show Table 13 which reports the concentrations (wt %) of the same four perfume compounds (ethyl-2-methyl butyrate, benzyl acetate, phenyl ethyl alcohol, cyclamen aldehyde) of the Model Perfume over time when tested as set forth in Inventive Sample B. FIG. 19 is the corresponding graphical plot.

Figures 20, 21:
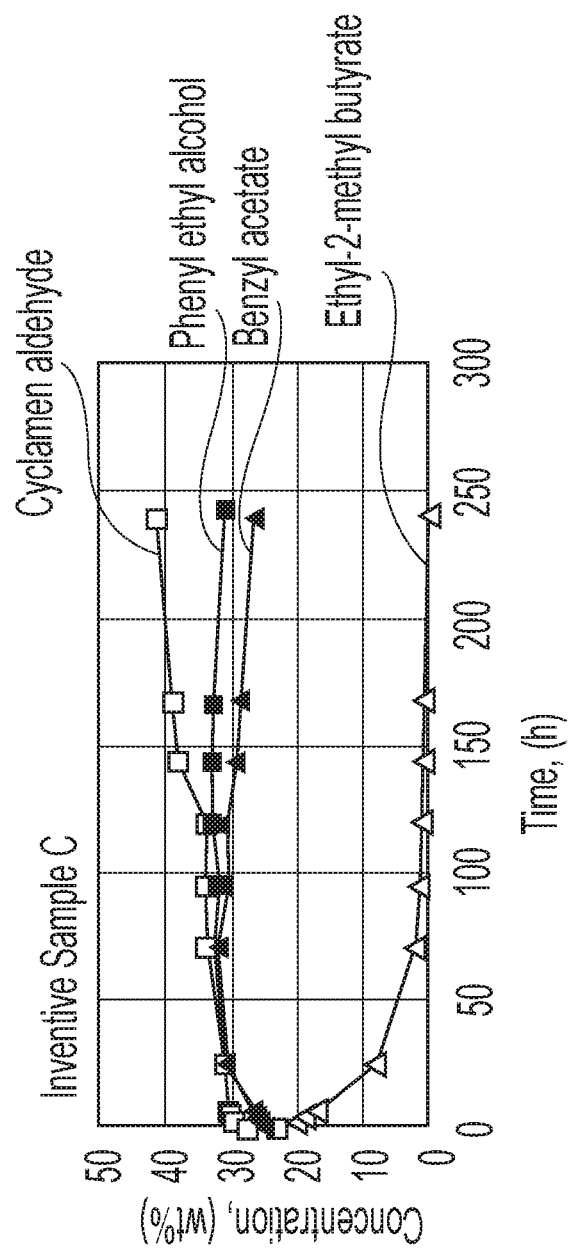
FIG. 20 illustrates Table 14 which reports concentrations (%) of volatile materials released from Inventive Sample C as a function of time.
FIG. 21 is a corresponding graph of Table 14 plotting concentration (%) of volatile materials released from Inventive Sample C as a function of time.

FIG. 20 show Table 14 which reports the concentrations (wt %) of the same four perfume compounds (ethyl-2-methyl butyrate, benzyl acetate, phenyl ethyl alcohol, cyclamen aldehyde) of the Model Perfume over time when tested as set forth in Inventive Sample C. FIG. 21 is the corresponding graphical plot.

Figures 22, 23:
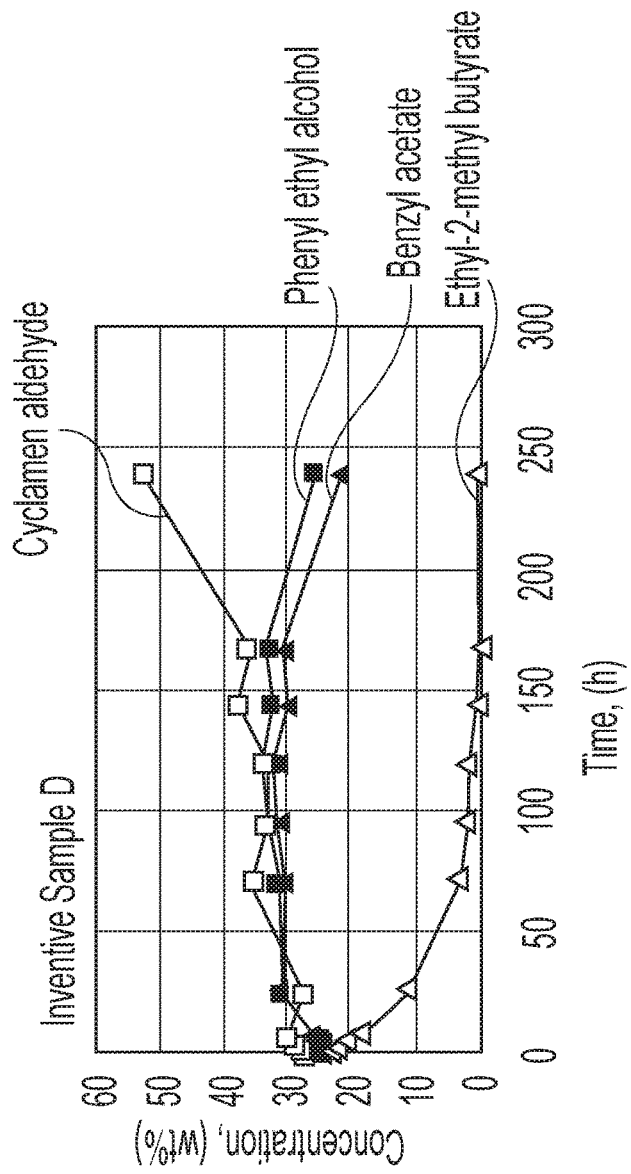
FIG. 22 illustrates Table 15 which reports concentrations (%) of volatile materials released from Inventive Sample D as a function of time.
FIG. 23 is a corresponding graph of Table 15 plotting concentration (%) of volatile materials released from Inventive Sample D as a function of time.

FIG. 22 show Table 15 which reports the concentrations (wt %) of the same four perfume compounds (ethyl-2-methyl butyrate, benzyl acetate, phenyl ethyl alcohol, cyclamen aldehyde) of the Model Perfume over time when tested as set forth in Inventive Sample D. FIG. 23 is the corresponding graphical plot.

Example IV

Example IV demonstrates that increasing a thickness of the second membrane 14 of the apparatus 1 may lead to a reduced vapor release rate of the volatile material. Table 16 describes the configuration of Samples used in Example IV. The vapor release rate of each of the following Samples are evaluated according to the Vapor Release Rate Test Method (Room) as described hereinbefore.

TABLE 16

| Material/Parameters | Comparative Sample D (Control) | Inventive Sample E | Inventive Sample F | Inventive Sample G |
|---|---|---|---|---|
| Perfume comprising common perfume raw materials including esters, ketones, aldehydes, and alcohols | 5.8 g | | | |
| Container for Perfume | Plastic Thermoform Container | | | |
| First Membrane (Wet Mode) | Polyethylene with silica Thickness = 279 μm | | | |
| Second Membrane (Dry Mode) | None | Polyethylene with silica | | |
| Thickness | — | 152 μm | 279 μm | 356 μm |
| Porosity | — | 60% | 60% | 60% |
| Pore size (μm) | — | 20 nm | 20 nm | 20 nm |

The Comparative Sample K and Inventive Samples D, E and F were placed in ambient laboratory conditions at 21° C. and the vapor release rate of the above samples was measured over 30 days according to Vapor Release Rate Test Method (Room). Table 17 below shows the vapor release rates and FIG. 24 is the corresponding graphical plot which shows the perfume release profiles of the above samples as a function of different thicknesses of the second membrane 14.

TABLE 17

| Time (Day) | Release rate (mg/cm$^2$-h) | | | |
|---|---|---|---|---|
| | Inventive Sample E | Inventive Sample F | Inventive Sample G | Comparative Sample K |
| 1 | 0.412 | 0.356 | 0.331 | 0.517 |
| 2 | 0.324 | 0.296 | 0.292 | 0.363 |
| 3 | 0.247 | 0.241 | 0.235 | 0.252 |
| 7 | 0.180 | 0.175 | 0.177 | 0.187 |
| 9 | 0.126 | 0.128 | 0.134 | 0.132 |
| 10 | 0.110 | 0.115 | 0.117 | 0.113 |
| 13 | 0.099 | 0.101 | 0.103 | 0.101 |
| 14 | 0.089 | 0.091 | 0.095 | 0.095 |
| 15 | 0.085 | 0.085 | 0.094 | 0.096 |
| 16 | 0.077 | 0.077 | 0.091 | 0.091 |
| 17 | 0.077 | 0.084 | 0.082 | 0.087 |
| 20 | 0.075 | 0.074 | 0.080 | 0.081 |
| 21 | 0.071 | 0.072 | 0.074 | 0.074 |
| 22 | 0.069 | 0.072 | 0.072 | 0.077 |
| 23 | 0.068 | 0.068 | 0.073 | 0.077 |
| 24 | 0.065 | 0.068 | 0.072 | 0.076 |
| 28 | 0.063 | 0.062 | 0.068 | 0.069 |
| 29 | 0.058 | 0.057 | 0.063 | 0.068 |
| 30 | 0.062 | 0.062 | 0.062 | 0.071 |

Figure 24:
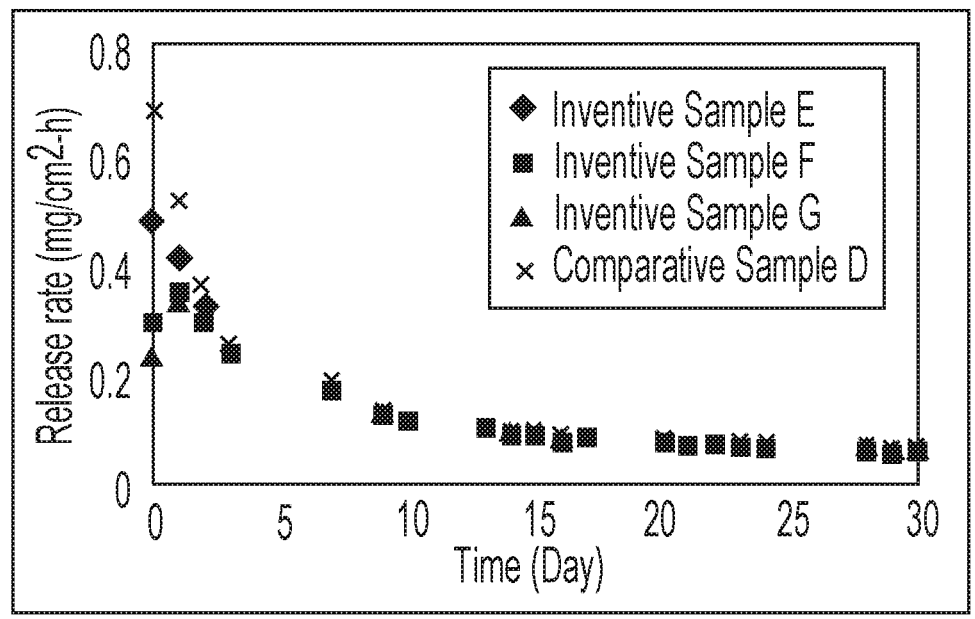
FIG. 24 is a graph plotting vapor release rates of volatile materials released from a conventional air freshener with a single membrane (Comparative Sample D) and apparatuses with second membranes of different mean thicknesses according to the present invention (Inventive Samples E, F and G) as a function of time.

Referring to Table 17 and FIG. 24, a significant reduction in initial perfume release rates (at 0 to 1 hours) was observed when the thickness of the membrane was increased. Also, for the samples tested, the greater the thickness of the membrane, the greater the reduction in initial perfume release rate verses the Comparative Sample K. Specifically, Inventive Sample G (thickest membrane) has a lower initial perfume release rate than Inventive Sample F (which has a lower initial perfume release rate than Inventive Sample E), and both Inventive Samples F, G have lower initial perfume release rates than Inventive Sample E (thinnest membrane).

Example V

Figure 25:
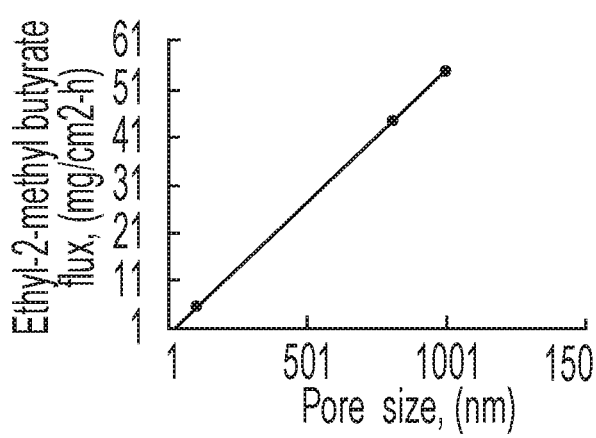
FIG. 25 is a graph plotting calculated vapor release rates of a volatile compound (ethyl-2-methyl butyrate) released from an apparatus for delivering a volatile material according to the present invention as a function of the mean pore size of the second membrane.
Figure 26:
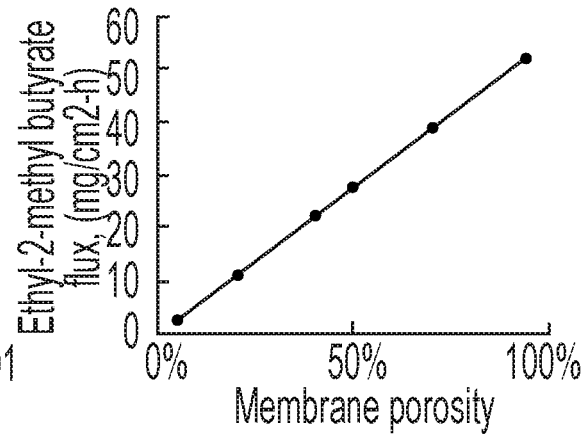
FIG. 26 is a graph plotting calculated vapor release rates of a volatile compound (ethyl-2-methyl butyrate) released from an apparatus for delivering a volatile material according to the present invention as a function of porosity of the second membrane.
Figure 27:
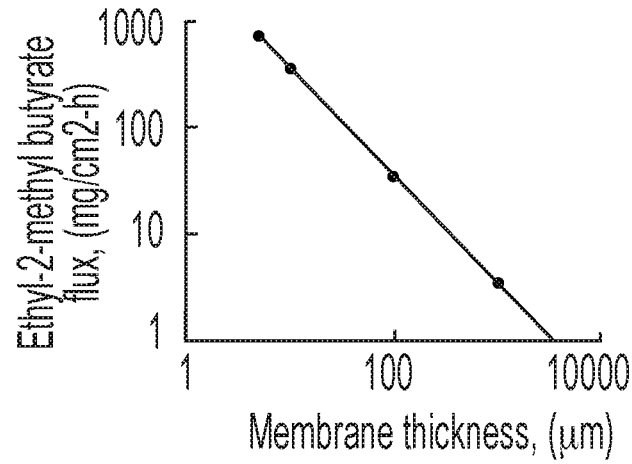
FIG. 27 is a graph plotting calculated vapor release rates of a volatile compound (ethyl-2-methyl butyrate) released from an apparatus for delivering a volatile material according to the present invention as a function of mean thickness of the second membrane.
Figure 28:
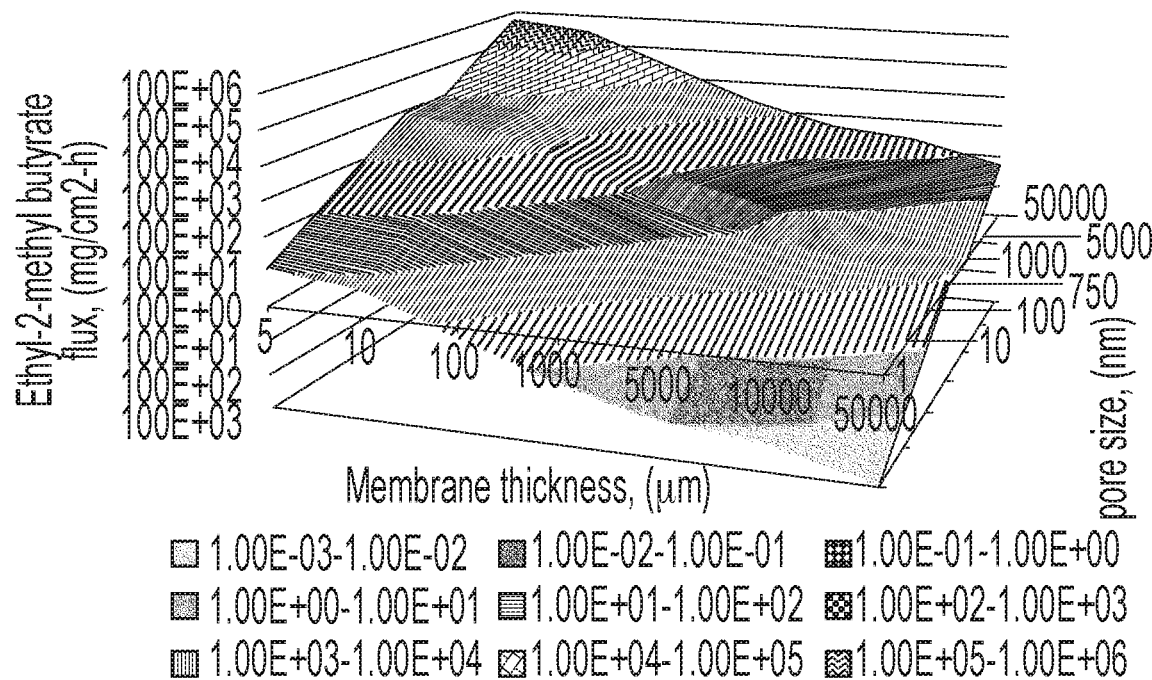
FIG. 28 is a graph plotting calculated vapor release rates of a volatile compound (ethyl-2-methyl butyrate) released from an apparatus for delivering a volatile material according to the present invention as a function of mean thickness and mean pore size of the second membrane.

Physical characteristics of a membrane (such as a second membrane) based on a desired vapor release rate (such as for example, a vapor release rate in the range of equal to or greater than 0.06 mg/cm$^2$-h and less than or equal to 4 mg/cm$^2$-h) may be determined by the Pore Size and Porosity Calculation Methods described hereinbefore. Referring to FIGS. 25, 26 and 27, the vapor release rate of the membrane increases linearly with the increase of mean pore size and porosity of the second membrane 14 but decreases linearly with the increase of membrane thickness. Based on the above relationship, the thickness, pore radius (r) and/or the porosity of the second membrane 14 may be configured singly or as a combination of parameters to obtain a desired vapor release rate. FIG. 28 is a graph plotting calculated vapor release rates of a volatile compound (ethyl-2-methyl butyrate) released from an apparatus for delivering a volatile material according to the present invention as a function of mean thickness and mean pore size of the second membrane.

For example, based on the release rate of 41.65 mg/cm-h at 25° C. for a perfume compound, i.e. ethyl-2-methyl butyrate, in a single membrane system (i.e. Comparative Sample A), the second membrane 14 may be configured to obtain a vapor release rate lower than 41.65 mg/cm2-h. Specifically, the second membrane 14 may comprise at least one of: a thickness of 0.001 mm to 10 mm, a pore radius (r) of less than 50,000 nm, a porosity of 0% to 95% by volume, based on the total volume of the second membrane 14.

Table 18 shows different combinations of a second membrane having different membrane thickness and pore sizes wherein the porosity of the second membrane is 50% and the tortuosity is 2.

TABLE 18

| Ethyl-2-methyl butyrate vapor flux (mg/cm$^3$-h) | Membrane thickness, (μm) | | | | | | |
|---|---|---|---|---|---|---|---|
| Pore size, r (nm) | 5 | 10 | 100 | 1000 | 5000 | 10000 | 50000 |
| 1 | 5.49 | 2.74 | 0.274 | 0.027 | 0.005 | 0.003 | 0.001 |
| 10 | 54.9 | 27.4 | 2.74 | 0.274 | 0.055 | 0.027 | 0.005 |
| 100 | 549 | 274 | 27.4 | 2.74 | 0.549 | 0.274 | 0.055 |
| 750 | 4116 | 2058 | 206 | 20.6 | 4.12 | 2.058 | 0.412 |
| 1000 | 5489 | 2744 | 274 | 27.4 | 5.49 | 2.74 | 0.549 |
| 5000 | 27443 | 13722 | 1372 | 137 | 27.4 | 13.7 | 2.74 |
| 50000 | 274431 | 137216 | 13722 | 1372 | 274 | 137 | 27.4 |

Table 19 below shows different combinations of a second membrane having different membrane thickness and pore sizes wherein the porosity of the second membrane is 30% and the tortuosity is 2.

TABLE 19

| Ethyl-2-methyl butyrate vapor flux (mg/cm$^3$-h) | Membrane thickness, (μm) | | | | | | |
|---|---|---|---|---|---|---|---|
| Pore size, r (nm) | 5 | 10 | 100 | 1000 | 5000 | 10000 | 50000 |
| 1 | 3.29 | 1.65 | 0.165 | 0.016 | 0.003 | 0.002 | 0.000 |
| 10 | 32.9 | 16.5 | 1.65 | 0.165 | 0.033 | 0.016 | 0.003 |
| 100 | 329 | 165 | 16.5 | 1.65 | 0.329 | 0.165 | 0.033 |

TABLE 19-continued

| Ethyl-2-methyl butyrate vapor flux (mg/cm³-h) | Membrane thickness, (μm) | | | | | | |
|---|---|---|---|---|---|---|---|
| Pore size, r (nm) | 5 | 10 | 100 | 1000 | 5000 | 10000 | 50000 |
| 750 | 2470 | 1235 | 123 | 12.3 | 2.47 | 1.235 | 0.247 |
| 1000 | 3293 | 1647 | 165 | 16.5 | 3.29 | 1.65 | 0.329 |
| 5000 | 16466 | 8233 | 823 | 82 | 16.5 | 8.2 | 1.65 |
| 50000 | 164659 | 82329 | 8233 | 823 | 165 | 82 | 16.5 |

Table 20 shows different combinations of a second membrane having different membrane thickness and pore sizes wherein the porosity of the second membrane is 95% and the tortuosity is 2.

TABLE 20

| Ethyl-2-methyl butyrate vapor flux (mg/cm³-h) | Membrane thickness, (μm) | | | | | | |
|---|---|---|---|---|---|---|---|
| Pore size, r (nm) | 5 | 10 | 100 | 1000 | 5000 | 10000 | 50000 |
| 1 | 10.43 | 5.21 | 0.521 | 0.052 | 0.010 | 0.005 | 0.001 |
| 10 | 104.3 | 52.1 | 5.21 | 0.521 | 0.104 | 0.052 | 0.010 |
| 100 | 1043 | 521 | 52.1 | 5.21 | 1.043 | 0.521 | 0.104 |
| 750 | 7821 | 3911 | 391 | 39.1 | 7.82 | 3.911 | 0.782 |
| 1000 | 10428 | 5214 | 521 | 52.1 | 10.43 | 5.21 | 1.043 |
| 5000 | 52142 | 26071 | 2607 | 261 | 52.1 | 26.1 | 5.21 |
| 50000 | 521420 | 260710 | 26071 | 2607 | 521 | 261 | 52.1 |

As shown in Table 19 (porosity=30%) and Table 20 (porosity=95%), increase in porosity of the second membrane 14 may increase the ethyl-2-methyl butyrate vapor flux linearly if the other membrane properties remain the same. For example, the maximum ethyl-2-methyl butyrate vapor flux through a second membrane with porosity at 30% (pore radius=10 nm, thickness=10 μm, tortuosity=2) is 16.5 mg/cm²-h for, and is lower than the evaporation rate of ethyl-2-methyl butyrate (41.65 mg/cm²-h) from the first membrane 13. However, an increase in porosity to 95% for the membrane may increase the maximum ethyl-2-methyl butyrate vapor flux through the second membrane to 52.1 mg/cm²-h and not reduce the evaporation rate of ethyl-2-methyl butyrate from the first membrane.

Example VI

Example VI demonstrate an effect of an air gap on the vapor release rate of an apparatus according to the present invention. Inventive Samples used in Example VI are based on the configuration of Inventive Sample A but differs in a distance of the air gap between the first and second membranes as determined by the Air Gap Measurement Method described hereinbefore and the properties of the second membrane as set out in Table 21 below. The vapor release rate of each of the following Samples are evaluated according to the Vapor Release Rate Test Method (Hood) as described hereinbefore.

TABLE 21

| Materials/Parameters | Comparative Sample | Inventive Sample | |
|---|---|---|---|
| | L | M | N |
| Second Membrane | Polyethylene, mean pore size = 3 nm | | |
| Air Gap | 0 mm | 4 mm | 12 mm |

Figure 29:
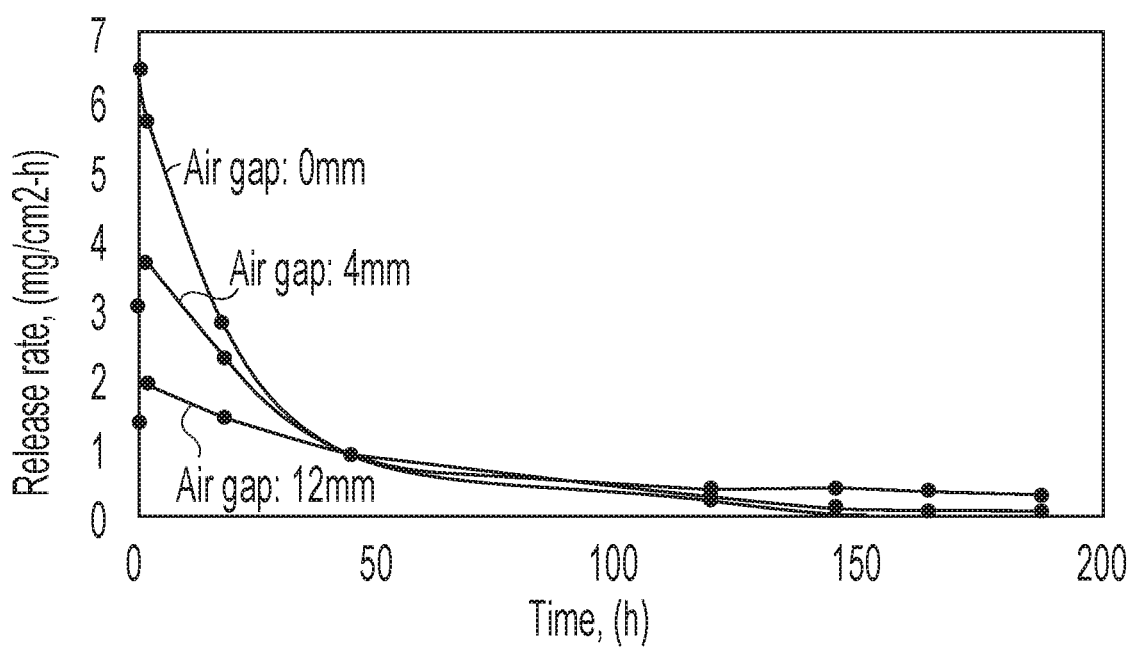
FIG. 29 is a graph plotting vapor release rates of an apparatus for delivering a volatile material according to the present invention as a function of an air gap between the first and second membranes.

FIG. 29 is a graphical plot showing results of Comparative Sample L and Inventive Samples M, N. As shown in FIG. 29, the vapor release rate of an apparatus 1 according to the present invention proportionally increases with the air gap. Comparative Sample L with no air gap, i.e. the space between the first and second membranes is 0 mm has a vapor release rate that is similar to a single membrane air freshener (such as for example Comparative Sample A). Specifically, when the first membrane 13 becomes wet, the vapor release rate may be dominated by the evaporation mode which is similar to the wet mode (demonstrated in Example I). On the other hand, the results of Inventive Samples M, N having an air gap of 4 mm and 12 mm respectively show that a higher air gap leads to a lower vapor release rate as the vapor needs to diffuse across a longer distance between the membranes before passing through the second membrane 14.

Example VII

Example VII demonstrate that air flow and temperature do not significantly affect a vapor release rate of an apparatus according to the present invention relative to conventional air fresheners such as Comparative Sample A (wet mode). Inventive Sample O used in Example VII is based on a similar configuration as Inventive Sample A and differs only in that a pure compound benzyl acetate is used as the volatile material and therefore will not be further described.

The vapor release rates of Comparative Sample A and Inventive Sample O are evaluated according to the Vapor Release Rate Test Method (Chamber) as described hereinbefore. Table 22 shows the vapor release rates of Inventive Sample O as a function of air velocity. FIG. 30 shows the vapor release rate of benzyl acetate as a function of air velocity when tested in accordance with Comparative Sample A. FIG. 31 is a corresponding graphical plot of Inventive Sample O.

TABLE 22

| Release rate (mg/cm²·h) | | Air velocity (m/s) | | | |
| --- | --- | --- | --- | --- | --- |
| | | 0.01 | 0.10 | 0.20 | 0.25 |
| Temperature (° C.) | 21 | 0.22 | 0.19 | 0.20 | 0.21 |
| | 30 | 0.47 | 0.39 | 0.43 | 0.44 |
| | 40 | 0.95 | 0.84 | 0.90 | 0.89 |

As shown in FIG. 31, at 40° C., 30° C. and 21° C., the configuration of Inventive Sample O demonstrates an overall reduced vapor release rate at each temperature. Further, the graph of FIG. 31 shows that the configuration of Inventive Sample O has a lower vapor release rate compared to the Comparative Sample A even with an increase in air velocity from 0.01 m/s to 0.25 m/s. Specifically, referring to the profiles for the Comparative Sample A (FIG. 30) and Inventive Sample O (FIG. 31) at 21° C., when air velocity rises from 0.01 m/s to 0.25 m/s, the profile of Inventive Sample O at 21° C. has a lower gradient relative to the profile of the Comparative Sample A at 21° C., which shows that the having a second membrane 14 and the vapor chamber 15 helps maintain a more constant vapor release rate than a configuration without a second membrane 14 and vapor chamber 15, despite variations in the air velocity around the apparatus 1. Therefore, a second membrane 14 and a vapor chamber 15 may be used to reduce the influence of air velocity and temperature on the vapor release rate of the volatile material from an apparatus, such as apparatus 1.

In an example, there is:

A. An apparatus for delivering a volatile material comprising:
   a reservoir for containing a volatile material, the reservoir including an opening;
   a first membrane disposed adjacent the opening of the reservoir; and
   a second membrane disposed adjacent the opening of the reservoir such that the first membrane is disposed between the reservoir and the second membrane, wherein at least a portion of the second membrane is spaced apart from the first membrane forming a vapor chamber between the first and second membranes.

B. The apparatus of A, wherein the first and second membranes are not in contact.

C. The apparatus of A or B, wherein the second membrane comprises a vapor release rate of greater than or equal to 0.06 mg/cm²·h and less than or equal to 4 mg/cm²·h at an air velocity of 0.1 m/s and a temperature of 25° C., wherein the vapor release rate is determined in accordance with the Vapor Release Rate Test Method specified within.

D. The apparatus of A, B or C, wherein the first membrane comprises a vapor surface area ($A_1$) and the second membrane comprises a vapor surface area ($A_2$), wherein $A_2$ is equal to or greater than $A_1$.

E. The apparatus of A, B, C or D, wherein at least a part of the second membrane comprises at least one of the following parameters: a mean thickness of 0.001 mm to 10 mm; a mean pore size of less than 50,000 nm; and a porosity of 5% to 95% by volume based on the total volume of the second membrane, the parameters measured in accordance with the respective Mean Thickness, Mean Pore Size, and Porosity Test Methods provided herein.

F. The apparatus of A, B, C or D, wherein at least a part of the second membrane comprises a mean pore size less than 2λ, wherein λ is a mean free path of vapor of the volatile material.

G. The apparatus according to F, wherein the mean pore size of the second membrane is in the range of 5 nm to 200 nm as determined by the Mean Pore Size Test Method specified herein.

H. The apparatus of any one of A to G, wherein the second membrane comprises a material selected from the group consisting of: paper, natural polymers, synthetic polymers and inorganic materials and mixtures thereof.

I. The apparatus of any one of A to H, further comprising a vapor impermeable substrate arranged within the apparatus to prevent release of the volatile material before activation.

J. The apparatus of I, wherein the vapor impermeable substrate is in contact with the second membrane.

K. The apparatus of I, wherein the vapor impermeable substrate is rupturable.

L. The apparatus of I, wherein the vapor impermeable substrate is adjacent to the first membrane and removably attached to an inner periphery of the side walls to form a sealed reservoir.

M. The apparatus of any one of A to L, wherein the volatile material comprises one or more perfume compounds, or a mixture of perfume compounds.

N. A method of delivering a volatile material into a space, the method comprising the steps of:
   (i) providing a volatile material in a reservoir;
   (ii) forming a vapor of the volatile material in a vapor chamber; and
   (iii) passing the vapor through a membrane comprising a first surface facing the vapor chamber and a second surface facing the atmosphere and away from the vapor chamber.

O. The method of N, further comprising, prior to step (iii), step (iv): passing a vapor phase or a liquid phase of the volatile material through a membrane disposed in the reservoir so as to form the vapor in the vapor chamber wherein the membrane of step (iv) is different from the membrane of step (iii).

P. The method of N or O, wherein the volatile material, the membrane and the vapor chamber are comprised in an apparatus according to A.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An apparatus for delivering a volatile material comprising:
   a reservoir for containing a volatile material, the reservoir including an opening;
   a first membrane disposed adjacent the opening of the reservoir; and
   a second membrane disposed adjacent the opening of the reservoir such that the first membrane is disposed between the reservoir and the second membrane, wherein at least a portion of the second membrane is spaced apart from the first membrane forming a vapor chamber between the first and second membranes, and wherein at least a part of the second membrane comprises a mean pore size less than $2\lambda$, wherein $\lambda$ is a mean free path of vapor of the volatile material.

2. The apparatus of claim 1, wherein the first and second membranes are not in contact.

3. The apparatus of claim 1, wherein the second membrane comprises a vapor release rate of greater than or equal to 0.06 mg/cm$^2$-h and less than or equal to 4 mg/cm$^2$-h at an air velocity of 0.1 m/s and a temperature of 25° C., wherein the vapor release rate.

4. The apparatus of claim 1, wherein the first membrane comprises a vapor surface area ($A_1$) and the second membrane comprises a vapor surface area ($A_2$), wherein $A_2$ is equal to or greater than $A_1$.

5. The apparatus of claim 1, wherein at least a part of the second membrane comprises at least one of: a mean thickness of 0.001 mm to 10 mm; a mean pore size of less than 50,000 nm; and a porosity of 5% to 95% by volume based on the total volume of the second membrane.

6. The apparatus according to claim 1, wherein the second membrane has a mean pore size in the range of 5 nm to 200 nm.

7. The apparatus of claim 1, wherein the second membrane comprises a material selected from the group consisting of: paper, natural polymers, synthetic polymers and inorganic materials and mixtures thereof.

8. The apparatus of claim 1, further comprising a vapor impermeable substrate arranged within the apparatus to prevent release of the volatile material before activation.

9. The apparatus of claim 8, wherein the vapor impermeable substrate is in contact with the second membrane.

10. The apparatus of claim 8, wherein the vapor impermeable substrate is rupturable.

11. The apparatus of claim 10, wherein the vapor impermeable substrate is adjacent to the first membrane and removably attached to an inner periphery of the side walls to form a sealed reservoir.

12. The apparatus of claim 1, wherein the volatile material comprises one or more perfume compounds, or a mixture of perfume compounds.

* * * * *